US008349781B2

(12) United States Patent
Artiga-Gonzalez et al.

(10) Patent No.: US 8,349,781 B2
(45) Date of Patent: Jan. 8, 2013

(54) FLUID RESERVOIR

(75) Inventors: Rene-Andres Artiga-Gonzalez, Düsseldorf (DE); Hubert Harth, Hilden (DE); Mario Sturm, Leverkusen (DE); Frank Korber, Düsseldorf (DE); Andreas Bauer, Kaarst (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/329,548

(22) Filed: Dec. 19, 2011

(65) Prior Publication Data

US 2012/0093902 A1 Apr. 19, 2012

Related U.S. Application Data

(60) Division of application No. 12/188,628, filed on Aug. 8, 2008, now Pat. No. 8,093,197, which is a continuation of application No. PCT/EP2006/012096, filed on Dec. 15, 2006.

(30) Foreign Application Priority Data

Feb. 8, 2006 (DE) ......................... 10 2006 005 988
May 8, 2006 (DE) ......................... 10 2006 021 553

(51) Int. Cl.

| | |
|---|---|
| ***A61K 8/00*** | (2006.01) |
| ***A61K 8/02*** | (2006.01) |
| ***A61K 9/14*** | (2006.01) |
| ***A61K 9/50*** | (2006.01) |
| ***C11D 17/00*** | (2006.01) |
| ***C11D 17/06*** | (2006.01) |
| ***C11D 3/37*** | (2006.01) |

(52) U.S. Cl. ........ 510/130; 510/136; 510/438; 510/441; 510/475; 424/401; 424/489; 424/502

(58) Field of Classification Search .................. 510/130, 510/136, 438, 441, 475; 424/401, 489, 502
See application file for complete search history.

(56) References Cited

U.S. PATENT DOCUMENTS

| | | | | | |
|---|---|---|---|---|---|
| 4,857,308 | A * | 8/1989 | Fukasawa et al. | 424/63 |
| 5,024,831 | A * | 6/1991 | Kurisaki et al. | 424/69 |
| 5,073,365 | A * | 12/1991 | Katz et al. | 427/2.24 |
| 5,336,665 | A * | 8/1994 | Garner-Gray et al. | 510/101 |
| 6,362,159 | B1 * | 3/2002 | Aguadisch et al. | 512/4 |
| 2005/0031699 | A1 * | 2/2005 | Simonnet et al. | 424/489 |

FOREIGN PATENT DOCUMENTS

WO WO 02/42364 A2 * 5/2002

* cited by examiner

*Primary Examiner* — Lorna M Douyon
(74) *Attorney, Agent, or Firm* — David K. Benson

(57) ABSTRACT

Fluid reservoirs which are based on polymer substrates and are capable of storing large amounts of fluids. The storage is reliable and the reemergence from the liquid reservoir is readily controllable, for example, via the temperature or via mechanical actions, to achieve retardation of the fluid release. Also, processes for producing such fluid reservoirs and also their use, for example in washing or cleaning compositions.

16 Claims, No Drawings

FLUID RESERVOIR

CROSS REFERENCE TO RELATED APPLICATIONS

This application is a divisional of U.S. application Ser. No. 12/188,628, filed on Aug. 8, 2008, now U.S. Pat. No. 8,093,197, which is a continuation under 35 U.S.C. §§120 and 365(c) of international application PCT/EP2006/012096, filed on Dec. 15, 2006. This application also claims priority under 35 U.S.C. §119 of DE 10 2006 005 988.3, filed on Feb. 8, 2006 and DE 10 2006 021 553.2, filed on May 8, 2006.

BACKGROUND OF THE INVENTION

The invention concerns a fluid reservoir based on a polymer substrate, its applications, and a process for manufacturing such fluid reservoir.

For many applications, there is a need for particulate carriers that can absorb fluids and, depending on the application, also store them and release them again when needed.

There are many models for this at the state of the art. As a general rule, certain core materials, such as zeolites, are impregnated with appropriate fluids, such as perfume oil. Often such a system is later coated to prevent undesired loss of the fluid.

DESCRIPTION OF THE INVENTION

There is, to be sure, a further need for corresponding systems that can absorb preferably even high proportions of fluids, store them reliably, and release them again only after a time delay. Satisfaction of such needs was the objective of this invention.

This objective was attained, surprisingly, by the subject of the invention. That is a particulate fluid reservoir made of a porous, particulate polymer substrate, which is charged with 5% by weight to 95% by weight, based on the total weight of the charged polymer substrate, of, an inclusion mixture. This inclusion mixture:

a) is, as such, highly viscous or solid at temperatures $\leqq 20°$ C., b) containing fluids, and contains at least one additive that can flow at elevated temperature, having a melting point or flow point in the range of 25° C. to 120° C., c) transforms, essentially without decomposition, into a molten state even at temperatures below 120° C.

The particulate fluid reservoir is, therefore, understood to be a porous polymer substrate in which high proportions of fluid, such are perfume, are immobilized reliably and stably. Release of the fluid can be accomplished, for instance, by temperature elevation and/or mechanical stress. Thus it is possible to create a sort of liquid depot that can be opened if needed.

The fluid reservoir can advantageously be incorporated into various matrices without a problem, even in liquid matrices, without there being any significant disadvantageous interaction with the matrix.

The concept "essentially without decomposition" takes into consideration the fact that many materials or compounds or substances can decompose due to input of thermal energy. That means that in such a case the material in consideration is so altered in its structure by the influence of the temperature that it is transformed into a state that is no longer suitable for its originally intended use.

In contrast, the inclusion mixtures are preferably distinguished by the fact that they transform into a molten state essentially without decomposition. That means that, at the particular temperature stress that is required to convert them to the molten state, they are not subject to any major degradation reactions, so that a inclusion mixture according to the invention preferably remains unaltered, in the greatest part, even after its transformation to a molten state and the subsequent transformation back into the solid state. That is in contrast to an object that suffers decompositions in transformation into the molten state, so that the object, after returning to the solid state, clearly differs from its initial condition, such as with respect to its appearance, its feel, its odor, or other aspects.

An inclusion mixture is preferably considered highly viscous if the Brookfield viscosity at 25° C. is greater than 2500 mPas, preferably 5,000 mPas, especially 7,500 mPas, preferably 10,000 mPas and particularly preferably 25,000 mPas. (Viscosity measurement in a Brookfield Model DV II Viscosimeter with Spindle 3 at 20 rpm).

The fluid is preferably a liquid (at T=20° C.), preferably comprising a) liquid fragrances (perfume oils and/or b) liquid ingredients of laundry detergents and cleaners, such as preferably surfactants, particularly nonionic surfactants, silicone oils, paraffins and/or c) liquid cosmetic ingredients, such as preferably oils, and/or d) liquid non-pharmaceutical additives or active ingredients and/or e) mixtures of the above.

Fragrances and nonionic surfactants are most highly preferred, especially in mixtures. In the sense of this invention, the terms "fragrance" and "perfume oil" are used synonymously. They mean, particularly, all those substances, or mixtures of them, which are perceived by humans and animals as odors, especially those perceived by humans as fragrances.

Individual fragrance compounds such as the synthetic products of the ester, ether, aldehyde, ketone, alcohol and hydrocarbon types can be used as perfume oils. Examples of ester-type fragrance compounds include, for example, benzyl acetate, phenoxyethyl isobutyrate, p-tert.-butylcyclohexyl acetate, linalyl acetate, dimethylbenzylcarbinyl acetate, phenylethyl acetate, linalyl benzoate, benzyl formate, ethyl methylphenyl glycinate, allylcyclohexyl propionate, styrallyl propionate and benzyl salicylate. The ethers include, for example, benzyl ethyl ether. The aldehydes include, for example, the linear alkanals with 8-18 C atoms, citral, citronellal, cittronellyloxyacetaldehyde, cyclamen aldehyde, hydroxycitronellal, lilial and bourgeonal. The ketones include, for example, the ionones, isomethylionone and methyl cedryl ketone. The alcohols include anethol, citronellol, eugenol, geraniol, linalool, phenylethyl alcohol and terpineol. The principal hydrocarbons are the terpenes and balsams. However, it is preferable to use mixtures of different fragrances which together produce a pleasant fragrance note.

The perfume oils can, obviously, also contain natural mixtures of fragrances, such as are available from plant or animal sources, such as pine, citrus, jasmine, lily, rose or ylang-ylang oil. Ethereal oils of low volatility that are used primarily as aroma components are also suitable perfume oils, such as sage oil, camilla oil, clove oil, melissa oil, mint oil, cinnamon leaf oil, linden blossom oil, juniper berry oil, vetiver oil, galbanum oil, and labdanum oil.

According to the invention, particular fragrances that can be used are selected from fragrances with (a) almond-like odor, such as preferably benzaldehyde, pentanal, heptenal, 5-methylfurfural, methylbutanal, furfural and/or acetophenone; or (b) apple-like odor, such as preferably (S)-(+)-ethyl 2-methylbutanoate, diethyl malonate, ethyl butyrate, geranyl butyrate, geranyl isopentanoate, isobutyl acetate, linalyl isopentanoate, (E)-β-damascone, heptyl 2-methylbutyrate, methyl 3-methylbutyrate, 2-hexenal pentylmethylbutyrate, ethylmethylbutyrate and/or methyl 2-methylbutanoate; or (c) apple-peel-like odor, such as preferably ethyl hexanoate, hexyl butanoate and/or hexyl hexanoate; or (d) apricot-like odor such as preferably γ-undecalactone, or (e) banana-like odor, such as preferably isobutyl acetate, isoamyl acetate, hexenyl acetate and/or pentyl butanoate; or (f) bitter-almond-like odor such as preferably 4-acetyltoluene, or (g) black-currant-like odor such as preferably mercaptomethyl pentanone and/or methoxymethylbutanethiol, or (h) citrus-like odor, such as preferably linalyl pentanoate, heptanal, linalyl isopentanoate, dodecanal, linalyl formate, α-p-dimethylstyrene, p-cymenol, nonanal, β-cubebene, (Z)-limonene oxide, cis-6-ethenyl-tetrahydro-2,2,6-trimethylpyran-3-ol, cis-pyranoid linalool oxide, dihydrolinalool, 6(10)-dihydromyrcenol, dihydromyrcenol, β-farnesene, (Z)-β-farnesene, (Z)-ocimene, (E)-limonene oxide, dihydroterpinyl acetate, (+)-limonene, (epoxymethylbutyl)-methylfuran and/or p-cymene; or (i) cocoa-like odor, such as preferably dimethylpyrazine, butyl methylbutyrate and/or methylbutanal; or (j) coconut-like odor, such as preferably γ-octalactone, γ-nonalactone, methyl laurate, tetradecanol, methyl nonanoate, (3S,3aS,7aR)-3a,4,5,7a-tetrahydro-3,6-dimethylbenzofuran-2(3H)-one, 5-butyldihydro-4-methyl-2-(3H)-furanone, ethyl undecanoate and/or δ-decalactone; or (k) cream-like odor such as preferably diethyl acetal, 3-hydroxy-2-butanone, 2,3-pentanedione and/or 4-heptanal; or (l) flower-like odor such as preferably benzyl alcohol, phenylacetic acid, tridecanal, p-anisyl alcohol, hexanol, (E,E)-farnesylacetone, methyl geranate, trans-crotonaldehyde, tetradecyl aldehyde, methyl anthranilate, linalool oxide, epoxylinalool, phytol, 10-epi-γ-eudesmol, nerol oxide, ethyl dihydrocinnamate, γ-dodecalactone, hexadecanol, 4-metcapto-4-methyl-2-pentanol, (Z)-ocimene, cetyl alcohol, nerolidol, ethyl (E)-cinnamate, elemicin, pinocarveol, α-bisabolol, (2R,4R)-tetrahydro-4-methyl-2-(2-methyl-1-propenyl)-1H-pyran, (E)-isoelemecin, methyl 2-methylpropanoate, trimethylphenyl butenone, 2-methylanisol, β-farnesol, (E)-isoeugeol, nitrophenylethane, ethyl vanillate, 6-methoxyeugenol, linalool, β-ionone, trimethylphenyl butenone, ethyl benzoate, phenylethyl benzoate, isoeugenol and/or acetophenone; or fresh odor, such as preferably methyl hexanoate, undecanone, (m) fresh odor, such as preferably methyl hexanoate, undecanone, (Z)-limonene oxide, benzyl acetate, ethyl hydroxyhexanoate, isopropyl hexanoate, pentadecanal, β-elemene, α-zingiberene, (E)-limonene oxide, (E)-p-mentha-2,8-dien-1-ol, menthone, piperitone, (E)-3-hexenol and/or carveol; or (n) fruit odor, such as preferably ethyl phenyacetate, geranyl valerate, γ-heptalactone, ethyl propionate, diethyl acetal, geranyl butyrate, ethyl heptanoate, ethyl octanoate, methyl hexanoate, dimethylheptenal, pentanone, ethyl 3-methylbutanoate, geranyl isovalerate, isobutyl acetate, ethoxypropanol, methyl-2-butenal, methyl nonanedione, linalyl acetate, methyl geranate, limonene oxide, hydrocinnamyl alcohol, diethyl succinate, ethylhexanoate, ethylmethylpyrazine, Nryletat, citronellyl butyrate, hexyl acetate nonyl acetate; butyl methylbutyrate, pentenal, isopentyldmethylpyrazine, p-menth-1-en-9-ol, hexadecanone, octyl acetate, γ-dodecalactone, epoxy-β-ionone, ethyl octenoate, ethyl isohexanoate, isobornyl propionate, cedrenol, p-menth-1-en-9-yl acetate, cadinadiene, (Z)-3-hexenyl hexanoate, ethyl cyclohexanoate, 4-methylthio-2-butanone, 3,5-octadienone, methyl cyclohexanecarboxylate, 2-pentyithiophene, α-ocimene, butanediol, ethyl valerate, pentanol, isopiperitone, butyl octanoate, ethyl vanillate, methyl butanoate, 2-methylbutyl acetate, propyl hexanoate, butyl hexanoate, isopropyl butanoate, spathulenol, butanol, δ-dodecalactone, methylquinoxaline, sesquiphellandrene, 2-hexenol, ethyl benzoate, isopropyl benzoate, ethyl lactate and/or citronellyl isobutyrate; or (o) geranium-like odor, such as preferably geraniol, (E,Z)-2,4-nonadienal, octadienone and/or o-xylene; or (p) grape-like odor, such as preferably ethyl decanoate and/or hexanone; or (q) grapefruit-like odor such as preferably (+)-5,6-dimethyl-8-isopropenylbicyclo[4.4.0]dec-1-en-3-one and/or p-menthenethiol; or (r) grass-like odor such as preferably 2-ethylpyridine, 2,6-dimethyl-naphthalene, hexanal, and/or (Z)-3-hexenol; or (s) green note, preferably 2-ethylhexanol, 6-decenal, dimethylheptenal, hexanol, heptanol, methyl-2-butenal, hexyl octanoate, nonanoic acid, undecanone, methyl geraniate, isobornyl formate, butanal, octanal, nonanal, epoxy-2-decenal, cis-linalool, pyrane oxide, nonanol, alpha,gamma-dimethylallyl alcohol, (Z)-2-penten-1-ol, (Z)-3-hexenyl butanoate, isobutylthiazol, (E)-2-nonenal, 2-dodecanal, (Z)-4-decenal, 2-octenal, 2-hepten-1-al, bicyclogermacrene, 2-octenal, α-thujene, (Z)-β-farnesene, (−)-γ-elemene, 2,4-octadienal, fucoserratene, hexenyl acetate, geranyl acetone, valencene, β-eudesmol, 1-hexenol, (E)-2-undecenal, Artemisia ketone, viridiflorol, 2,6-nonadienal, trimethylphenyl butenone, 2,4-nonadienal, butyl isothiocyanate, 2-pentanol, elemol, 2-hexenal, 3-hexenal, (+)-(E)-limonene oxide, cis-isocitral, dimethyloctadienal, bornyl formate, bornyl isovalerate, isobutyraldehyde, 2,4-hexadienal, trimethylphenyl butenone, nonanone, (E)-2-hexenal, (+)-cis-rosene oxide, menthone, coumarin, (epoxymethylbutyl)-methylfuran, 2-hexenol, (E)-2-hexenol and/or carvyl acetate; or (t) green-tea-like odor, preferably (−)-cubenol, or (u) herb-like odor, preferably octanone, hexyl octanoate, caryophyllene oxide, methylbutenol, safranal, benzyl benzoate, bornyl butyrate, hexyl acetate, β-bisabolol, piperitol, β-selinene, α-cubebene, p-menth-1-en-9-ol, 1,5,9,9-tetramethyl-12-oxabicyclododeca-4,7-diene, T-muuroloi, (−)-cubenol, levomenol, ocimene, α-thujene, p-menth-1-en-9-yl acetate, dehydrocarveol, Artemisia alcohol, γ-muurolene, hydroxypentanone, (Z)-ocimene, β-elemene, δ-cadinol, (E)-β-ocimene, (Z)-dihydrocarvone, α-cadinol, calamenene, (Z)-piperitol, lavandulol, β-bourbonene, (Z)-3-hexenyl 2-methylbutanoate, 4-(1-methylethyl)-benzenemethanol, Artemisia ketone, methyl-2-butenol, heptanol, (E)-dihyrocarvone, p-2-menthen-1-ol, α-curcumene, spathulenol, sesquiphellandrene, citronellyl valerate, bornyl isovalerate, 1,5-octadiene-3-ol, methyl benzoate, 2,3,4,5-tetrahydroanisol and/or hydroxycalamenene; or (v) honey-like odor, preferably ethyl cinnamate, β-phenylethyl acetate, phenylacetic acid, phenylethanal, methyl anthranilate, cinnamic acid, β-damascenone, ethyl-(E)-cinnamate, 2-phenylethyl alcohol, citronellyl valerate, phenylethyl benzoate and/or eugenol; or (w) hyacinth-like odor, preferably hotrienol, or (x) jasmine-like odor, preferably methyl jasmonate, methyl dihydroepijasmonate and/or methyl epijasmonate, or
(y) lavender-like odor, preferably linalyl valerate and/or linalool, or
(z) citron-like odor, preferably neral, octanal, δ-3-carene, limonene, geranial, 4-mercapto-4-methyl-2-pentanol, citral, 2,3-dihydro-1,8-cineol and/or α-terpinene; or
(aa) lily-like odor, preferably dodecanal, or
(bb) magnolia-like odor, preferably geranyl acetone, or
(cc) mandarin-like odor, preferably undecanol, or
(dd) melon-like odor, preferably dimethylheptenal, or
(ee) mint-like odor, preferably menthone, ethyl salicylate, p-anisaldehyde, 2,4,5,7a-tetrahydro-3,6-dimethylbenzofuran, epoxy-p-menthene, geranial, (methylbutenyl)-methylfuran, dihydrocarvyl acetate; β-cyclocitral, 1,8-cineol, β-phellandrene, methylpentanone, (+)-limonene, dihydrocarveol, (−)-carvone, (E)-p-mentha-2,8-dien-1-ol, isopulegyl acetate. piperitone, 2,3-dihydro-1,8-cineol, α-terpineol, DL-carvone and/or α-phellandrene, or
(ff) nut-like odor, preferably 5-methyl-(E)-2-hepten-4-one, γ-heptalactone, 2-acetylpyrrol, 3-octen-2-one, dihydromethylcyclopentapyrazine, acetylthiazol, 2-octenal, 2,4-heptadienal, 3-octenone, hydroxypentanone, octanol, dimethylpyrazine, methylquinoxaline and/or acetylpyrroline; or
(gg) orange-like odor, preferably methyl octanoate, undecanone, decyl alcohol, limonene and/or 2-decenal; or
(hh) orange-peel-like odor, preferably decanal and/or β-carene; or
(ii) peach-like, preferably γ-nonalactone, (Z)-6-dodecene-γ-lactone, δ-decalactone, R-δ-decenolactone, hexyl hexanoate, 5-octanolide, γ-decalactone and/or δ-undecalactone; or
(jj) peppermint-like odor, preferably methyl salicylate and/or I-menthol; or
(kk) pine-like flavor, preferably α-p-dimethylstyrene, β-pinene, bornyl benzoate, δ-terpinene, dihdroterpinyl acetate and/or α-pinene; or
(ll) pineapple-like odor, preferably propyl butyrate, propyl propanoate and/or ethyl acetate; or
(mm) plum-like odor, preferably benzyl butanoate; or
(nn) raspberry-like odor, preferably β-ionone, or
(oo) rose-like odor, preferably β-phenethyl acetate, 2-ethylhexanol, geranyl valerate, geranyl acetate, citronellol, geraniol, geranyl butyrate, geranyl isovalerate, citronellyl butyrate, citronellyl acetate, isogeraniol, tetrahydro-4-methyl-2-(2-methyl-1-propenyl)-2,5-cis-2H-pyran, isogeraniol, 2-phenylethyl alcohol, citronellyl valerate and/or citronellyl isobutyrate; or
(pp) green mint-like odor, preferably carvyl acetate and/or carveol; or
(qq) strawberry-like odor, preferably hexylmethyl butyrate, methyl cinnamate, pentenal, methyl cinnamate; or
(rr) sweetish odor, preferably benzyl alcohol, ethylphenyl acetate, tridecanal, nerol, methyl hexanoate, linalyl isovalerate, undecanaldehyde, carophyllene oxide, linalyl acetate, safranal, uncineol, phenylethanal, p-anisaldehyde, eudesmol, ethylmethylpyrazine, citronellyl butyrate, 4-methyl-3-penten-2-one, nonyl acetate, 10-epi-γ-eudesmol, β-bisabolol, (Z)-6-dodecen-γ-lactone, β-farnesene, 2-dodecanal, γ-dodecalactone, epoxy-β-ionone, 2-undecenal, styrene glycol, methyl furaneol, (−)-cis-rosene oxide, (E)-β-ocimene, dimethylmethoxyfuranone, 1,8-cineole, ethylbenzaldehyde, 2-pentylthiophene, α-farnesene, methionol, 7-methoxycoumarin, (Z)-3-hexenyl-2-methylbutanoate, o-aminoacetophenone, viridiflorol, isopiperitone, β-sinensal, ethyl vanillate, methyl butanoate, p-methoxystyrene, 6-methoxyeugeol, 4-hexanolid, δ-dodecalactone, sesquiphellandrene, diethylmalate, linalyl butyrate, guaiacol, coumarin, methyl benzoate, isopropyl benzoate, safrole, durene, γ-butyrolactone, ethyl isobutyrate and/or furfural; or
(ss) vanilla-like odor, preferably vanillin, methyl vanillate, acetovanillone and/or ethyl vanillate; or
(tt) watermelon-like odor, preferably 2,4-nordienal, or
(uu) wood-like odor, preferably α-muurolene, cadina-1,4-dien-3-ol, isocaryophyllene, eudesmol, α-ionone, bornyl butyrate, (E)-α-bergamotene, linalool oxide, ethylpyrazine, 10-epi-γ-eudesmol, germacrene B, trans-sabinene hydrate, dihydrolinalool, isodihydrocarveol, β-farnesene, β-sesquiphellandrene, d-elemene, α-calacorene, epoxy-β-ionone, germacrene D, bicyclogermacrene, alloaromadendrene, α-thujene, oxo-β-ionone, (−)-γ-elemene, γ-muurolene, sabinene, α-guainene, α-copaene, γ-cadinene, nerolidol, β-eudesmol, α-cadinol, δ-cadinene, 4,5-dimethoxy-6-(2-propenyl)-1,3-benzodioxol, [1ar-(1a-alpha, 4a alpha, 7 alpha, 7a beta 7b alpha)]-decahydro-1,1,7-trimethyl-4-methylene-1H-cycloprop[e]azulene, α-gurjunene, guaiol, α-farnesene, γ-selinene, 4-(1-methylethyl)-benzenemethanol, perillene, elemol, α-humulene, b-caryophyllene and/or β-guaiene;

or mixtures of the above.

The fluid is preferably an essentially hydrophobic liquid. Typical hydrophobic groups are, for example, long-chain or aromatic hydrocarbon groups. Perfume oils are as a general rule hydrophobic liquids.

The fluid can preferably contain liquid cosmetic ingredients, such as oils. Preferred oils can advantageously be completely synthetic oils such as silicone oils, vegetable and/or animal fat oils triglycerides of medium or unsaturated fatty acids) and/or ethereal oils (such as from plant parts).

The inclusion mixture, advantageously the fluid, can preferably contain one or more skin-care and/or skin-protective active substances.

Skin-care active substances are all those active substances that give the skin a sensory and/or cosmetic advantage. Active skin-care substances are preferably selected from the following substances:

a) waxes, such as, for example, carnauba, spermaceti, beeswax, lanolin and/or derivatives of those and others
b) hydrophobic plant extracts
c) hydrocarbons, such as squalene and/or squalane
d) higher fatty acids, preferably those with at least 12 carbon atoms, such as lauric acid, stearic acid, behenic acid, myristic acid, palmitic acid, oleic acid, linoleic acid, linolenic acid, isostearic acid and/or multiply unsaturated fatty acids and others
e) higher fatty alcohols, preferably those with at least 12 carbon atoms, such as lauryl alcohol, cetyl alcohol, stearyl alcohol, oleyl alcohol, behenyl alcohol, cholesterol and/or 2-hexadecanol and others
f) esters, preferably those such as cetyl octanoate, lauryl lactate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactates, alkyl citrates and/or alkyl tartrates and others.
g) lipids, such as, for example, cholesterol, ceramide and/or sucrose esters and others
h) vitamins such as Vitamins A and E, vitamin alkyl esters, including Vitamin C alkyl esters and others
i) sunscreens
j) phospholipids k) derivatives of alpha-hydroxyacids l) odorants m) germicides for cosmetic use, both synthetic such as salicylic acid and/or others, as well as natural ones such as neem oil and/or others.

n) silicones and mixtures of components named above.

The inclusion mixture, advantageously the fluid, can preferably contain oil with antiseptic action, preferably ethereal oil, selected in particular from the group of Angelica fine—*Angelica archangelica, Anis—Pimpinella anisum, Benzoe siam—Styrax tokinensis, Cabreuva—Myrocarus fastigiatus, Cajeput—Melaleuca leucadendron, Cistrose—Cistrus ladaniferus, Copaiba balsam—Copaifera reticulata*, costus root—Saussurea discolor, silver fir needles—*Abies alba*, elemi—*Canarium luzonicum*; fennel—*Foeniculum dulce*; spruce—*Picea abies*; geranium—*Pelargonium graveolens*; ho leaves—*Cinnamonum camphora*; immortelle (straw flowers)—*Helichrysum ang.*; ginger extra—*Zingiber off.*; Saint John's wort—*Hypericum perforatum*; jojoba, German camomile—*Matricaria recutita*; blue fine camomile: *Matricaria chamomilla; Roman camomile: Anthemis nobilis*; wild camomile: *Ormensis multicaulis*; carrot: *Daucus carota*; dwarf pine—*Pinus mugho*; lavender: *Lavendula hybrida; Litsia cubeba*—(May Chang), *Manuka—Leptospermum scoparium; melissa—Melissa officinalis*; maritime pine—*Pinus pinaster*; myrrh—*Commiphora molmol*; myrtle—*Myrtis communis*; neem—*Azadirachta; Niaouli*—(MQV) *Melaleuca quin. viridiflora*; palmarosa—*Cymbopogom martini*; patchouli—*Pogostemon patschule; Peru balsam—Myroxylon balsmaum var. pereirae*; raventsara aromatics, rose wood—*Aniba rosae odora*, sage—*Salvia officinalis*; horsetail—*Equisetaceae*; milfoil extra—*Achille millefolia*; ribwort plantain—*Plantago lanceolata*; styrax—*Liquidambar orientalis*; French marigold (marigold)—*Tagetes patula*; tea tree—*Melaleuca alternifolia*; tolu balsam—*Myroxylon balsamum L.*; Virginia cedar—*Juniperus virginiana*; frankincense (Olibanum)—*Boswellia carteria*; silver fir—*Abies alba.*

The inclusion mixture, advantageously the fluid, can preferably contain skin-protective active substances, advantageously skin-protecting oil. The skin-protecting substance is advantageously a skin-protecting oil, for example, also a carrier oil, particularly selected from the group of algal oil, *Oleum phaeophyceae*, Aloe vera oil, Aloe vera brasiliana, apricot kernel oil, *Prunus armeniaca*, arnica oil, *Arnica montana*, avacodo oil *Persea americana*, borage oil *Borago officianalis*, calendula oil *Calendula officinalis*, camellia oil *Camellia oleifera*, thistle oil *Carthaqmus tinctorius*, peanut oil *Arachis hypogaea*, hemp oil *Cannabis sativa*, hazelnut oil *Corylus avellana*, Saint John's wort oil *Hypericum perforatum*, jojoba oil *Simondsia chinensis*, carrot oil *Daucus carota*, coconut oil *Cocos nucifera*, pumpkin seed oil *Curcubita pepo*, kukui nut oil *Aleurites moluccana*, macadamia nut oil *Macadamia ternifolia*, almond oil *Prunus dulcis*, olive oil *Olea europaea*, peach seed oil *Prunus persica*, rapeseed oil *Brassica oleifera*, castor oil *Ricinus communis*, nutmeg oil *Nigella sativa*, sesame oil *Sesamium indicum*, sunflower oil *Helianthus annus*, grapeseed oil *Vitis vinifera*, walnut oil *Juglans regia*, wheat germ oil *Triticum sativum*, with borage oil, hemp oil and almond oil particularly advantageous of these.

The inclusion mixture, advantageously the fluid, can preferably contain humidity control factors, such as those selected from the following group: amino acids, chitosan or chitosan salts/derivatives, ethylene glycol, glucosamine, glycerol, diglycerol, triglycerol, uric acid, honey and hardened honey, creatinine, hydrolysis products of collagen, lactitol, polyols and polyol derivatives (such as butylene glycol, erythritol, propylene glycol, 1,2,6-hexanetriol, polyethylene glycols such as PEG-4, PEG-6, PET-7, PEG-8, PEG-9, PEG-10, PEG-12, PEG-14, PEG-16, PEG-18, PEG-20), pyrrolidine carboxylic acid, sugars and sugar derivatives (such as fructose, glucose, maltose, maltitol, mannitol, inositol, sorbitol, sorbityl silanediol, sucrose, trehalose, xylose, xylitol, glucuronic acid and its salts), ethoxylated sorbitol (Sorbeth-6, Sorbeth-20, Sorbeth-30, Sorbeth-40), hardened starch hydrolysates and mixtures of hardened wheat protein and PEG-20-acetate copolymer, especially panthenol.

According to a preferred embodiment the polymer substrate is hydrophobic.

According to a further preferred embodiment, the longitudinal diameter of the fluid reservoir, measured at its longest dimension, is between 20 um and 30 cm. Lower limits can also be 30 μm, 40 μm, 50 μm, 60 μm, 70 um, 80 μm or 100 μm, or even higher values such as 200 μm, 300 μm, 400 μm, 500 μm, 600 μm, etc. Upper limits can also be 20 cm, 15 cm, 10 cm, 5 cm, 3 cm, 1 cm, 0.5 cm, 0.25 cm, 0.1 cm or 0.01 cm or even lower values such as 0.005 cm, etc.

According to a preferred embodiment the polymer substrate is at least partially built up of polymers selected from polyolefins, fluoropolymers, styrene polymers, copolymers of those polymers and/or mixtures of the polymers named above.

For example, polypropylenes, polyethylenes, etc. are particularly preferred. Hydrophobic polymer substrates are used preferably. HDPE, LDPE, LLDPE, or UHMW-PE are particularly advantageous polyethylenes. Poly(4-methyl-1-pentene), poly(1-butene) or polyisobutene are particularly preferred, and, as copolymers, ethylene-propylene copolymers or ethylene-vinyl acetate copolymers. Examples of preferred fluoropolymers include polyvinylidene fluoride and polyvinyl fluoride and the copolymers poly(tetrafluoroethylene-co-hexafluoropropylene), poly(tetrafluoroethylene-co-perfluoroalkyl vinyl ether) and poly(ethylene-co-tetrafluoroethylene). Of the styrene polymers, polystyrene and styrene-acrylonitrile copolymers, styrene-butadiene copolymers and acrylonitrile butadiene styrene copolymers are preferred. However, polymer substrates based on polyolefins, and especially based on polypropylene or polyethylene are particularly preferred. In particular, cross-linked (co-)polymers are likewise preferred.

According to a preferred embodiment, the polymer substrate has at least partially an open-pore structure with a mean pore diameter preferably between 1 μm and 300 μm before charging with the inclusion mixture. The lower limit can also have values such as 5 μm, 10 μm, 15 μm, 20 μm, 25 μm or 30 μm, etc. The upper limits can also be at values such as 280 μm, 260 μm, 240 μm or 220 μm, etc.

A usable porous particulate polymer substrate with at least partially open-pore structure can have a spongy cellular or even a network-like or coral-like microstructure. The pore structure should be at least partially open-pore. That is, the pores in the polymer substrate must be in fluid contact with each other, at least in subregions of the substrate structure, and the particles of the polymer substrate should be open-pored in at least subregions of their external surface. That allows adequate permeability to the fluids. Thus use of a particulate polymer substrate with at least partial open-pore structure allows extensive fluid uptake. In a preferred embodiment the polymer substrate used according to the invention has a mean pore diameter in the range between 4 and 110 μm. A mean pore diameter in the range of 5 to 50 μm is especially preferred. Polymer substrates with such preferred pore diameters exhibit good charging ability.

According to a preferred embodiment the inclusion mixture transforms essentially without decomposition into a molten state at temperatures below 100° C., advantageously below 90° C., in an advantageous manner below 80° C., especially below 70° C.

According to a further preferred embodiment, the inclusion mixture comprises at least 20% by weight, preferably at least 30% by weight, advantageously at least 40% by weight, in a very advantageous manner at least 50% by weight, in an especially advantageous manner at least 60% by weight, in an extremely advantageous manner at least 70% by weight, in the utmost advantageous manner at least 80% by weight, in an even more advantageous manner at least 90% by weight, particularly at least 95% by weight, but in the most advantageous manner 100% by weight of the components fluid and additive(s) having melting points or flow points in the range of 25° C. to 120° C.

According to another preferred embodiment the additives contained in the inclusion mixture having a melting point or flow point in the range of 25° C. to 120° C. are at least partially soluble in the fluid, preferably essentially completely soluble in the fluid near their particular flow point.

According to another preferred embodiment the inclusion mixture is highly viscous or particularly solid at temperatures up to ≦22° C., advantageously up to ≦28° C., in a very advantageous manner up to ≦32° C., in a particularly advantageous manner up to ≦38° C., in a quite particularly advantageous manner up to ≦42° C., in a further advantageous manner up to ≦48° C., in a still further advantageous manner up to ≦55° C., in an even more advantageous manner up to ≦60° C.

According to a further preferred embodiment, the flow point of the additive that is able to flow at elevated temperatures, or of the mixture of these additives, is greater than 25° C., preferably in the range of 30 to 90° C., advantageously in the range of 35 to 70° C. and particularly in the range of 40 to 60° C.

According to a further preferred embodiment, the inclusion mixture comprises up to 90% by weight, preferably 10 to 80% by weight, but especially preferably less than 70% by weight, that is, advantageously 15 to 65% by weight, in a very advantageous manner up to 55% by weight, in an even more advantageous manner 28 to 50% by weight of additives that are able to flow at elevated temperatures (that is, additives with flow points or melting points in the range of 25° C. to 120° C.), based on the total inclusion mixture with which the polymer substrate is charged.

According to a further preferred embodiment, the inclusion mixture comprises more than 5% by weight of fluid(s), preferably more than 10% by weight, advantageously 15 to 90% by weight, in a very advantageous manner 20 to 80% by weight, in an even more advantageous manner 25 to 75% by weight, especially 30 to 72% by weight of fluid(s), based on the total inclusion mixture with which the polymer substrate is charged.

According to a further preferred embodiment, the fluid reservoir contains less than 25% by weight, preferably less than 15% by weight, advantageously less than 10% by weight, even more advantageously less than 5% by weight of water, based on the total fluid reservoir, and in particular it is completely free of water.

According to a further preferred embodiment, the additives contained in the inclusion mixture, which have flow points in the temperature range of 25° C. to 120° C., are selected from the group of fatty alcohols, fatty acids, silicones (silicone oils), paraffins, nonionic surfactants, esterquats, glycerides of fatty acids (natural oils), waxes, mono, di or tri-glycerides, carbohydrates and/or polyalkylene glycols.

As carbohydrates, sugars can be used here to advantage. Some examples are alpha-D-glucose monohydrate (melting point in the range of 83-86° C.), alpha-D-galactose monohydrate (melting point in the range of 118-120° C.) or maltose monohydrate (melting point in the range of 102-103° C.). The derivatives are also suitable, for instance, amino sugars such as D-glucosamine (melting point of the $\alpha$-form: 88° C.) or deoxysugars such as rhamnose monohydrate (melting point 92-94° C.).

Suitable paraffins can be, for instance, octadecane, nonadecane, eicosane, docosane, tricosane, tetracosane, pentacosane, hexacosane, octacosane, nonacosane or triacosan, to name some examples.

Suitable fatty alcohols can be, for instance, 1-tridecanol, 1-tetradecanol, 1-pentadecanol, 1-hexadecanol, 1-heptadecanol, 1-octadecanol, 9-trans-octadecen-1-ol, 1-nonadecanol, 1-eicosanol, 1-heneicosanol, 1-docosanol, 12-cis-docosen-1-ol, or 3-trans-docosen-1-ol, to name some examples. They also include the so-called wax alcohols, fatty alcohols with about 24-36 carbon atoms, such as triacontanol-1 or melissyl alcohol. They also include unsaturated fatty alcohols such as elaidyl alcohol, eruca alcohol or brassidyl alcohol. They also include Guerbet alcohols such as $C_{32}H_{66}O$ or $C_{36}H_{74}O$. They also include alkanediols such as undecane-1,11-diol or dodecane-1,12-diol.

Suitable nonionic surfactants can be, for instance, fatty alcohol polyglycol ethers, such as $C_{14}H_{29}$—O—$(CH_2CH_2O)_2H$, $C_{10}H_{21}$—O—$(CH_2CH_2O)_8H$, $C_{12}H_{25}$—O—$(CH_2CH_2O)_6H$, $C_{14}H_{29}$—O—$(CH_2CH_2O)_4H$, $C_{16}H_{33}$—O—$(CH_2CH_2O)_{12}H$, or $C_{18}H_{37}$—O—$(CH_2CH_2O)_4H$, to name some examples.

Suitable fatty acids can be, for instance, capric acid, undecanoic acid, lauric acid, tridecanoic add, tetradecanoic acid, pentadecanoic acid, palmitic acid, margaric acid, stearic acid, nonadecanoic acid, arachidic acid, behenic acid, lignoceric acid, cerotinic acid, crotonic acid, erucic acid, eleostearic acid, or melissic acid, to name some examples.

Esters of fatty acids, such as the methyl or ethyl esters of behenic or arachidic acid can also be suitable, to name some examples.

Mono, di or triglycerides, such as the corresponding glycerides of lauric acid, palmitic acid or capric acid, are also suitable, to name some examples.

Suitable waxes can be natural waxes such as carnauba wax, candelilla wax, esparto wax, guaruma wax, Japan wax, cork wax or montane wax; also animal waxes such as beeswax, wool wax, shellac wax or spermaceti wax; also synthetic waxes such as polyalkylene waxes or polyethylene glycol waxes, likewise chemically modified waxes such as hydrogenated jojoba wax or montane ester wax.

The inclusion mixture can also contain other additional substances having a melting point above 120° C., such as appropriate carbohydrates, advantageously sugars, such as sucrose (melting point 185-186° C.).

If the inclusion mixture contains other solids, preferably solids commonly used in laundry detergents, that is likewise a preferred embodiment.

If the proportion of solids in the inclusion mixture is less than 50%, preferably less than 30%, advantageously less than 25%, especially less than 15%, in an entirely preferred manner less than 10%, based on the total inclusion mixture with which the polymer substrate is charged, this is a further preferred embodiment.

According to a preferred embodiment the solids contained in the inclusion mixture have a d50 value of less than 0.2 mm, preferably less than 0.1 mm, especially less than 0.05 mm.

If the inclusion mixture contains solids selected from the group of zeolites, bentonites, silicates, phosphates, urea and/or its derivatives, sulfates, carbonates, citrates, citric acid, acetates and/or salts of the anionic surfactants, this is a further preferred embodiment:

According to a further preferred embodiment, the fluid reservoir has a size such that it can be grasped by human hands and can be used for manual treatment of objects. For instance, one can rub surfaces with a fluid reservoir in stick form, as in hand washing of textiles.

The fluid reservoir can have any desired form. It can preferably be rather spherical, oval, cylindrical, or granular, or have any other regular or irregular shape.

A fluid reservoir that contains at least one, preferably two or more substances usually contained in laundry detergents or cleaners, preferably a substance from the group of surfactants, builder substances (inorganic and organic builders), bleaching agents, bleach activators, bleach stabilizers, bleach catalysts, enzymes, special polymers (for example, those with co-builder properties), antiredeposition agents, optical brighteners, UV-protecting substances, soil repellents, electrolytes, coloring agents, odorants, scents, perfume carriers, pH-adjusting agents, complexing agents, fluorescence agents, foam inhibitors, anti-wrinkling agents, antioxidants, quaternary ammonium compounds, antistatics, ironing aids, UV absorbers, antiredeposition agents, germicides, antimicrobially active substances, fungicides, viscosity regulators, luster agents, color transfer inhibitors, shrinkage inhibitors, corrosion inhibitors, preservatives, plasticizers, softening rinses, protein hydrolysates, phobing and impregnating agents, hydrotropes, silicone oils as well as anti-swelling and anti-slip agents, is a preferred embodiment of the invention.

It turns out that preferably the following proportions, each based on the total fluid reservoir proportions, each based on the total fluid reservoir, can be particularly advantageous:

- porous polymer substrate: preferably 40-75% by weight, especially 40-60% by weight
- fluid in the polymer substrate: preferably 1-30% by weight, especially 20-30% by weight
- additive that can flow at elevated temperatures: preferably 1-30% by weight, especially 20-30% by weight The fluid reservoir according to the invention is characterized advantageously by the fact that high proportions of liquid, such as perfume, for instance, are reliably immobilized for long periods in the porous polymer substrate and are not released until there is an external stimulus, such as a temperature increase and/or mechanical stress.

Although the external, visible, surface of the polymer substrate can preferably be occupied by the inclusion mixture, so that one can also advantageously speak of a coated polymer substrate, it is further possible according to a preferred embodiment to give the fluid reservoir according to the invention, that is, the polymer substrate charged with the inclusion mixture, an additional coating. According to a preferred embodiment of the invention, the fluid reservoir is coated.

Coating agents can be used for the coating. These are substances that give the outer surface of the object to be coated a glossy appearance and/or form a coating (an envelope) on the outer surface. Solid and/or liquid substances can be used as coating agents. They are preferably those that prevent or delay penetration of moisture or prevent or delay loss of aroma.

Suitable coating agents can contain water-soluble, water-dispersible and/or water-insoluble (co)-polymers. The layer of coating itself can be soluble or insoluble in water.

Water soluble polymers contain a proportion of hydrophilic groups sufficient for water solubility, and are advantageously not cross-linked. The hydrophilic groups can be nonionic, anionic, cationic or zwitterionic, for instance: $-NH_2$, $-OH$, $-SH$, $-O-$, $-COOH$, $-COO-^{-M+}$, $-SO_3^{-M+}$, $-PO_3^{-2}M^{+2}$, $-NH_3^+$.

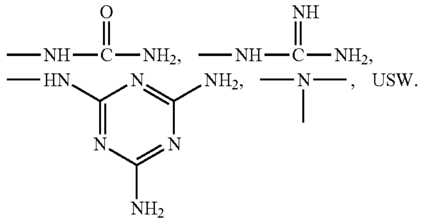

USW.

etc.

The individual polymers can contain different hydrophilic groups at the same time, such as ionic and nonionic and/or anionic and cationic groups.

Preferred water-soluble polymers can be, for example, natural polysaccharides and/or peptides, such as starches, alginates, pectins, plant gums, caseins, gelatins, etc.

Preferred water-soluble polymers can be, for example, semisynthetic polymers, such as cellulose ethers or starch ethers.

Preferred water-soluble polymers can be, for example, biotechnologically produced products, such as pullulan, curdlan or xanthan.

Preferred water-soluble polymers can be, for example, synthetic polymers, such as homopolymers and/or copolymers of (meth)acrylic acid and its derivatives, of maleic acid, vinylsulfonic acid, vinylphosphonic acid, polyvinyl alcohol, polyethyleneimine, polyvinylpyrrolidone and the like.

Preferred coating agents contain water-soluble (co)-polymers, especially those having a melting point or softening point in the range of 48° C. to 300° C., advantageously in the range of 48° C. to 200° C., and in a further advantageous manner in the range of 48° C. to 200° C.

Suitable water-soluble (co)-polymers with an appropriate melting or softening point can advantageously be selected from the group comprising polyalkylene glycols, polyethylene terephthalates, polyvinyl alcohols and mixture of them.

The coating can contain, aside from the actual coating agent, or independently of it, other ingredients, such as, advantageously, textile-softening compounds and/or perfume.

It is also possible to coat the fluid reservoir multiply, such as by first coating the fluid reservoir with a first coating, e. g., one containing a textile-softening compound and then giving the resulting object a further coating, such as one containing water-soluble polymer and perfume.

According to a preferred embodiment the coating of the fluid reservoir comprises lipids and/or silicone oils. Preferred lipids are (a) lipophilic hydrocarbons (such as triacontane, squalene or carotenoids, etc.)

(b) lipophilic alcohols (such as wax alcohols, retinol or cholesterol, etc.)

(c) ether lipids (d) lipophilic carboxylic acids (fatty acids)

(e) lipophilic esters [such as neutral fats—that is, monoacyl glycerols, diacyl glycerols, triacyl glycerols (triglycerides), sterol esters, etc.]
(f) lipophilic amides (such as ceramides, etc.)
(g) waxes
(h) lipids having more than 2 hydrolysis products, such as glycolipids, phospholipids, sphingolipids and/or glycerolipids, etc.
(i) lipids in the form of higher-molecular-weight conjugates having more than 2 hydrolysis products, such as lipoproteins and/or lipopolysaccharides, etc.
(j) phosphorus-free glycolipids, such as glycosphingolipids (such as, preferably, cerebrosides, gangliosides, sulfatides) or such as glycoglycerolipids (such as preferably glycosyldiglycerides and glycosylmonoglycerides), etc.
(k) carbohydrate-free phospholipids, such as sphingophospholipids (such as preferably sphingomyelins) or such as glycerophospholipids (such as preferably lecithins, cephalins, cardiolipids, phosphatidyl inositol and phosphatidyl inositol phosphates, etc.)
(l) mixtures of those named above.

In a further preferred embodiment, the optional coating has colored substances or dyes, brighteners and/or pigments, advantageously in the nanoscale range or in the micrometer range, preferably white pigments, particularly selected from titanium dioxide pigments, such as, in particular, anatase pigments and/or rutile pigments, zinc sulfide pigments, zinc oxide (zinc white), antimony trioxide (antimony white), basic lead carbonate (white lead), $2PbCO_3.Pb(OH)_2$, or lithopone, $ZnS+BaSO_4$. It can preferably also contain white additives such as preferably calcium carbonate, talc, $3MgO.4SiO_2.H_2O$ and/or barium sulfate.

In a further preferred embodiment, the pigments that can preferably be components of an optional coating can be
(a) colored pigments (preferably inorganic colored pigments, especially iron oxide pigments, chromate pigments, iron blue pigments, chromium oxide pigments, ultramarine pigments, pigments of oxide solid solution pigments and/or bismuth vanadate pigments.
(b) black pigments (e. g., aniline black, perylene black, iron oxide pigments, manganese black and/or spinel black)
(c) luster pigments (preferably lamellar effect pigments, metal effect pigments such as aluminum pigments (silver bronze), copper pigments and copper/zinc pigments (gold bronzes) and zinc pigments, pearlescent pigments, such as magnesium stearate, zinc stearate, lithium stearate or ethylene glycol distearate or polyethylene terephthalate, interference pigments such as metal oxide mica pigments) and/or
(d) luminescent pigments such as azomethine fluorescent yellow, silver-dosed and/or copper-dosed zinc sulfide pigments.

The optional coating can preferably also comprise the following substances:
(a) carbonates, such as preferably chalk, ground limestone, calcite and/or precipitated calcium carbonate, dolomite and/or barium carbonate
(b) sulfates, such as preferably barite, blanc fixe and/or calcium sulfate.
(c) silicates such as preferably talc, pyrophyllite, chlorite, hornblende, mica, or kaolin
(d) silicic acids, such as preferably quartz, fused silica, cristobalite, diatomaceous earth, Neuberg silica, precipitated silicic acid, pyrogenic silicic acid, ground glass, pumice flour, perlite, calcium metasilicate and/or fibers from melts of glass, basalts, or slags
(e) oxides, such as especially aluminum hydroxide and/or magnesium hydroxide
(f) (organic fibers, such as especially textile fibers, cellulose fibers, polyethylene fibers, polypropylene fibers, polyamide fibers, polyacrylonitrile fibers and/or polyester fibers, especially with lengths in the nanometer or micrometer range and/or
(g) powders, such as powdered starch.

According to a further preferred embodiment, the optional coating of the fluid reservoir according to the invention is sensitive to pH and/or temperature and/or ionic strength or contains materials sensitive to pH and/or temperature and/or ionic strength.

The term 'pH sensitivity, temperature sensitivity and/or ionic strength sensitivity' means here that the coating or the materials making up the coating
(a) experience(s) a change (increase or decrease) of solubility (preferably in water); and/or
(b) experience(s) a change (increase or decrease) of the diffusion density; and/or
(c) experience(s) a change (acceleration or deceleration) of the rate of dissolution; and/or
(d) experience(s) a change (increase or decrease) of mechanical stability if there is a change if the pH, the temperature, or the ionic strength of the medium to which the coating is exposed (e. g., a wash liquor).

For the temperature sensitivity, there is, aside from the options (a) to (d) named above also the additional option (e) according to which the coating or the materials making up the coating experience(s) a change of the state of aggregation from solid to liquid or the reverse on a change of the temperature; that is, the materials melt or solidify.

In the sense of the invention, all those materials for which the integrity is a function of the temperature and/or the pH and/or the ionic strength, or also those materials that lose their integrity because of mechanical stress, such as occurs in the coarse of an automatic laundry washing process serve as suitable materials.

The pH sensitivity of the (optional) coating can be utilized advantageously. The (optional) coating can, for example, be of such a nature that it dissolves, partially or completely, if the pH drops below a critical level. That can occur in a laundering process, for instance, if the alkaline wash water is removed from the machine and fresh water is supplied to the machine, preferably in the rinsing portion of the washing process. Then on contact with the fresh water the coating partially or completely loses its integrity, making the granulation penetrable by the water. The particular pH at which the coating disintegrates partially or completely can be adjusted arbitrarily, so that, for example, the material loses its integrity partially or completely if, for example, the pH drops below 9.0 but remains essentially inert as long as the pH is greater than 10.

The concept "inert" is to be understood according to the invention in the usual sense, that is, that there is essentially no physical or chemical reaction of the material of the coating with its environment but that the material of the coating is physically and chemically resistant to it, so that the granulation is essentially protected from penetration of the environment, such as the wash liquor.

Preferred coating materials can be
(a) polymers containing carboxylate groups (polycarboxylates), preferably homopolymers of acrylic acid and/or copolymers of acrylic acid and maleic acid, (b) polyethylene glycols, especially those having molecular weights less than about 25,000 g/mole, preferably less than about 10,000 g/mole, advantageously less than about 6,000 g/mole, such as PEG 4000,
(c) (acetalized) polyvinyl alcohols
(d) (modified) carbohydrates, preferably mono-, oligo-, and/or poly-saccharides, especially glucose
(e) polyvinylpyrrolidones
or mixtures of those.

"Polyvinyl alcohols" (abbreviated PVAL, or occasionally also PVOH) is the designation for polymers having the general structure $$[—CH_2—CH(OH)—]_n$$

which also contain in small proportions structural units of the type $$[—CH_2—CH(OH)—CH(OH)—CH_2]$$

The usual commercial polyvinyl alcohols, which are marketed as yellowish-white powders or granulations having degrees of polymerization in the range of about 100 to 2500 (molecular weights of about 4,000 to 100,000 g/mole) have degrees of hydrolysis of 98-99 or 87-89 mole-%, thus containing a residual content of acetyl groups. Manufacturers characterize the polyvinyl alcohols by stating the degree of polymerization of the initial polymer, the degree of hydrolysis, the saponification number, or the viscosity of the solution.

Depending on their degree of hydrolysis, polyvinyl alcohols are soluble in water and the less polar organic solvents (formamide, dimethylformamide or dimethylsulfoxide). They are not attacked by (chlorinated) hydrocarbons, esters, fats and oils. Polyvinyl alcohols are classifed as toxicologically unobjectionable and are at least partially biodegradable. The water solubility can be reduced by post-treatment with aldehydes (acetalization), complexing with nickel or copper salts, or treatment with dichromates, boric acid or borax. Polyvinyl alcohol coatings are largely impermeable to gases such as oxygen, nitrogen, helium, hydrogen or carbon dioxide, but allow water vapor to penetrate.

In the context of the present invention, those coatings are preferred that comprise, at least in part, a polyvinyl alcohol with a degree of hydrolysis advantageously 70 to 100 mole % preferably 80 to 90 mole-%, especially preferably 81 to 89 mole-%, and particularly 82 to 88 mole-%. In a preferred embodiment the film material used comprises at least 20% by weight, especially preferably at least 40% by weight, quite particularly preferably at least 60% by weight, and particularly at least 80% by weight of a polyvinyl alcohol for which the degree of hydrolysis is 70 to 100 mole-%, preferably 80 to 90 mole-%, especially preferably 81 to 89 mole-%, and particularly 82 to 88 mole-%. It is preferable for the total coating to contain at least 20% by weight, especially preferably at least 40% by weight, quite particularly preferably at least 60% by weight and particularly at least 80% by weight of a polyvinyl alcohol for which the degree of hydrolysis is 70 to 100 mole-%, preferably 80 to 90 mole-%, especially preferably 81 to 89 mole-%, and particularly 82 to 88 mole-%.

Polyvinyl alcohols of a particular molecular weight molecular range are used preferably as coating materials. It is preferred according to the invention that the film material comprise a polyvinyl alcohol having a molecular weight in the range of 10,000 to 100,000 g/mol, preferably 11,000 to 90,000 g/mol, especially preferably 12,000 to 80,000 g/mol, and particularly 13,000 to 70,000 g/mol.

The polyvinyl alcohols described above are broadly available commercially, as under the Mowiol® trade name (Clariant). Polyvinyl alcohols particularly suitable in the context of the present invention include, for example, Mowiol® 3-83, Mowiol® 4-88, Mowiol® 5-88, Mowiol® 8-88 and L648, L734, Mowiflex LPTC 221 from KSE and compounds from Texas Polymers, such as Vinex 2034.

Other polyvinyl alcohols that are especially suitable as coating materials can be found in the table below:

| Designation | Degree of hydrolysis [%] | Molecular weight [kDa] | Melting point [° C.] |
|---|---|---|---|
| Airvol ® 205 | 88 | 15-27 | 230 |
| Vinex ® 2019 | 88 | 15-27 | 170 |
| Vinex ® 2144 | 88 | 44-65 | 205 |
| Vinex ® 1025 | 99 | 15-27 | 170 |
| Vinex ® 2025 | 88 | 25-45 | 192 |
| Gohsefimer ® 5407 | 30-28 | 23,600 | 100 |
| Gohsefimer ® LL02 | 41-51 | 17,700 | 100 |

Other polyvinyl alcohols suitable as coating materials are ELVANOL® 51-05, 52-22, 50-42, 85-82, 75-15, T-25, T-66, 90-50 (DuPont trademarks), ALCOTEX® 72.5, 78, B72, F80/40, F88/4, F88/26, F88/40, F88/47 (trademarks of Harlow Chemical Co.), Gonozoïde® NK-05, A-300, AH-22, C-500, GH-20, GL-03, GM-14L, KA-20, KA-500, KH-20, KP-06, N-300, NH-26, NM11Q, KZ-06 (trademarks of Nippon Gohsei K. K.). ERKOL types from Wacker are also suitable.

The water-solubility of PVAL can be altered by post-treatment with aldehydes (acetalization) or ketones (ketalization). Polyvinyl alcohols that have been acetalized or ketalized with the aldehyde or ketone groups of saccharides or polysaccharides or mixture of them have proven particularly advantageous because of their outstandingly good solubility in cold water and are specially preferred. The reaction products of PVAL and starch are used as extremely advantageous.

The water solubility can be further altered by complexing with nickel or copper salts or by treatment with dichromates, boric acid, or borax, so that it can be adjusted deliberately to desired values. Films of PVAL are largely impermeable to gases such as oxygen, nitrogen, helium, hydrogen, and carbon dioxide, but allow water vapor to penetrate.

Other preferred coating materials are characterized in that they comprise polyvinylpyrrolidones. Polyvinylpyrrolidones, abbreviated PVP, can be described by the following general formula

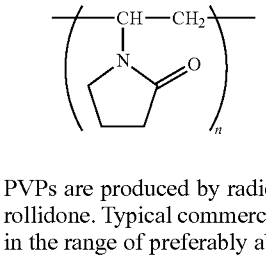

PVPs are produced by radical polymerization of 1-vinylpyrrolidone. Typical commercial PVPs have molecular weights in the range of preferably about 2,500 to 750,000 g/mol and are marketed as white hygroscopic powders or as aqueous solutions.

Other preferred coating materials are characterized in that they comprise polyethylene oxides. Polyethylene oxides, abbreviated PEOX, are polyalkylene glycols having the general formula $$H—[O—CH_2—CH_2]_n—OH$$

They are produced industrially by base-catalyzed polyaddition of ethylene oxide (oxirane) with ethylene glycol as the starting molecule in systems usually containing traces of water. They have molecular weights in the range of about 200 to 5,000,000 g/mol, and corresponding degrees of polymerization of about 5 to >100,000. Polyethylene oxides have an extremely low concentration of reactive hydroxyl terminal groups, and have only weak properties of glycols.

Other preferred coating materials are characterized in that they comprise gelatins. Gelatin is a polypeptide (molecular weight: about 15,000 to >250,000 g/mol) obtained primarily by hydrolysis of collagen contained in animal skin and bones under acidic or alkaline conditions. The amino acid composition of gelatin largely corresponds to that of the collagen from which it was obtained, and varies, depending on the source.

Coating materials that comprise a polymer from the group of starches and starch derivatives, cellulose and cellulose derivatives, especially methylcellulose and mixture of those are preferred in the context of the present invention.

Starch is a homoglycan, in which the glucose units are joined by α-glycoside bonds. Starch is composed of two components having different molecular weights: about 20 to 30% straight-chain amylose (molecular weight about 50,000 to 150,000) and 70 to 80% branched-chain amylopectin (molecular weight about 300,000 to 2,000,000). It also contains traces of lipids, phosphoric add and cations. While amylose forms long intertwined chains of about 300 to 1,200 glucose molecules because of the 1,4 bonding, the amylopectin chain branches through 1,6 bonds after an average of 25 glucose units, giving a branch-like structure with about 1,500 to 12,000 glucose molecules. Starch derivatives that can be obtained by polymer-like reactions of starch are also suitable, along with pure starch, for producing water-soluble envelopes in the context of the present invention. For example, such chemically modified starches comprise products of esterifications or etherifications, in which hydroxyl hydrogen atoms are substituted. However, starches in which the hydroxyl groups are replaced by functional groups not bound through an oxygen atom can also be used as starch derivatives. The group of starch derivatives includes, for example, alkali starches, carboxymethylstarch (CMS), starch esters and starch ethers, as well as amino starches.

Pure cellulose has the empirical formula $(C_6H_{10}O_5)_n$. Considered formally, it is a β-1,4-polyacetal of cellobiose, which is itself made up of two molecules of glucose. Suitable celluloses consist of about 500 to 5,000 glucose units, and accordingly have average molecular weights of 50,000 to 500,000. In the context of the present invention, cellulose derivatives that can be obtained from cellulose by polymer-like reactions are usable as disintegrants based on cellulose. Such chemically modified celluloses include, for example, products of esterifications or etherifications in which hydroxyl hydrogen atoms are replaced. However, celluloses in which the hydroxyl groups are replaced by functional groups not bound through oxygen atoms can also be used as cellulose derivatives. The group of cellulose derivatives includes, for example, alkali celluloses, carboxymethylcellulose (CMS), cellulose esters and ethers, and amino celluloses.

A further object of the present invention is a process for producing a fluid reservoir according to the invention, in which one brings a mixture of additives that are highly viscous or solid at T≦20° C., and fluids, to a liquid state by heating, mixes this flowable mixture with a porous polymer substrate, and then lets it cool.

In this way the accessible pore system of the polymer substrate can be fully charged if necessary and the pores can also be sealed preferably by cooling after charging.

A process for producing a fluid reservoir in which a) one or more common fluids at temperatures of 20 to 22° C. are mixed by stirring with additive(s) having a flow point in the range of 20° C. to 100 C and then b) the mixture is heated to temperatures in the range of the flow point of the additive, preferably above the flow range, so that a flowable mixture results, and then c) while retaining the elevated temperature, other optional additives, especially the usual additives for laundry detergents, advantageously selected from the group of zeolites, bentonites, silicates, phosphates, urea and/or its derivatives, sulfates, carbonates, citrates, citric acid, acetates and/or salts of anionic surfactants are suspended in the mixture, with the mixture still flowable, and then d) the flowable mixture is mixed with a porous polymer substrate at temperatures of 25° to 50° C., and finally e) the resulting mixture is allowed to cool is a preferred embodiment of the invention.

If the polymer is preheated to a temperature of 25°-150° C. before it is mixed with the flowable mixture, that is a preferred embodiment.

In a preferred embodiment the cooling of the mixture is accelerated by adding cold.

According to a preferred embodiment of the invention it is also possible to suspend the ingredients of an inclusion mixture according to the invention, comprising odorants in particular, and the porous particulate polymer substrate and optionally other additives in liquid carbon dioxide ($CO_2$), mixing them (further) there, and then removing the liquid carbon dioxide, by, for example, simply reducing the pressure in the system so that vaporization can occur. If the expansion of the carbon dioxide is intentionally slowed, particularly advantageous fluid reservoirs can be produced. It is advantageous to work with liquid carbon dioxide in a pressure range of 20 bar to 70 bar at 20° C. Carbon dioxide can likewise be used in other pressure ranges and temperature ranges as long as it is liquid under those conditions.

Laundry detergents or cleaners containing fluid reservoirs according to the invention, and likewise a cosmetic containing fluid reservoirs according to the invention are an extremely preferred subject of the present invention.

Use of the fluid reservoirs according to the invention, especially in the form of fragrance blocks and/or fragrance bags for odorizing rooms, vehicles, or closets is likewise a further preferred subject of the invention.

Use of the fluid reservoirs according to the invention for odorizing objects, preferably laundry detergents, washing machines and cleaning machines, dry laundry and packages is likewise a further preferred subject of the invention.

Use of the fluid reservoirs according to the invention for odorizing textiles during the washing or drying process, preferably done by machine, is likewise a further preferred subject of the invention.

Use of the fluid reservoirs according to the invention for direct manual treatment of objects, preferably for rubbing on the objects, especially in manual washing of objects, is likewise a further preferred subject of the invention.

For instance, fluid reservoirs that hold ingredients of manual dishwashing agents, selected, for example, from (a) surfactants, such as alkane sulfonates, alkyl ether sulfates, alkyl polyglucosides and/or cocoamidopropyl-betaine, advantageously those suitable for wetting the material being washed and the dirt, removal of grease and other contaminants, (b) (organic) acids, such as citric acid, advantageously suitable for adjusting the pH and for influencing drainage, (c) hydrotropes, such as cumene sulfonate, advantageously suited to avoid phase separation,
(d) fat replacers, such as fatty acid amides, advantageously suitable for replacing skin fat,
(e) care ingredients, such as Aloe vera extracts, advantageously suitable for skin care,
(f) fragrances (perfume),
(g) dyes
(h) substances with antibacterial action, such as sodium benzoate or sodium salicylate, advantageously suitable for reducing the microbial load.
(l) preservatives.

For instance, fluid reservoirs may be preferred that contain ingredients of machine dishwashing agents, selected, for example, from the following:

phosphates, such as pentasodium triphosphate, phosphonates, citrates, such as sodium citrate, sodium polycarboxylates, sodium metasilicate, soda, sodium bicarbonate, sodium disilicate, active chlorine, sodium perborate, bleach activator, such as TAED, enzymes, such as proteases and amylases, (low-foam) nonionic surfactants, silver and glass protection, odorants.

For example, fluid reservoirs may be preferred which contain ingredients of textile detergents, for instance, selected from the following:

anionic surfactants, such as preferably alkylbenzenesulfonate and/or alkyl sulfate, nonionic surfactants such as preferably fatty alcohol polyglycol ether, alkyl polyglucoside and/or fatty acid glucamide, builders, such as preferably zeolite, polycarboxylate and/or sodium citrate, alkalies, such as preferably sodium carbonate, alcohols such as preferably ethanol and/or glycerol, bleaching agents such as preferably sodium perborate and/or sodium percarbonate, corrosion inhibitors such as preferably sodium silicate, stabilizers, such as preferably phosphonates, foam inhibitors such as preferably soaps, silicone oils and/or paraffins, enzymes such as preferably proteases, amylases, cellulases, and/or lipases, antiredeposition agents such as preferably carboxymethylcellulose, discoloration inhibitors such as preferably polyvinylpyrrolidone derivatives, adjusting agents such as preferably sodium sulfate, odorants, optical brighteners, such as preferably stilbene derivatives and/or biphenyl derivatives, and water.

For example, fluid reservoirs may be preferred which contain ingredients of all-purpose cleaners, selected, for instance, from the following:

surfactants, such as alkane sulfonates, alkylbenzenesulfonates, alkyl polyglucosides, fatty alcohol polyglycol ether sulfates, fatty alcohol polyglycol ethers, builders such as trisodium citrate, the sodium salt of nitrilotriacetic acid, sodium phosphonate, pentasodium triphosphate, solvents and hydrotropes (solubilizers), such as ethanol, propylene glycol ether, sodium toluene or cumene sulfonate, odorants, colorants, or preservatives. Acidic all-purpose cleaners contain acids, such as preferably acetic acid, citric or maleic acid. All-purpose cleaners adjusted to be (weakly) alkaline contain alkalies, such as preferably sodium hydroxide or soda [sodium carbonate].

Use of the fluid reservoir according to the invention as toilet blocks is likewise another preferred subject of the invention. A toilet block according to the invention, for hanging in the toilet bowl or flush tank, for instance, can release small amounts of acids, surfactant and/or fragrance and thus slow the deposition of contaminants.

A further subject of the invention is a product such as preferably a household sponge, rag or towel, with which at least one surface of the product is filled with firmly attached fluid reservoirs. For example, it is advantageous to have a scouring sponge having its scouring side occupied by the fluid reservoirs. When used manually, fluid is released from the reservoir due to the mechanical stress, so that, if the fluid is perfume, a pleasant odor is produced.

As was discussed previously, a fluid reservoir that contains at least one, preferably two or more substances typically contained in laundry detergents or cleaners is a preferred embodiment of the invention. Furthermore, a fluid reservoir according to the invention that contains a laundry detergent or cleaner is a highly preferred subject of the present invention. In the following, therefore, ingredients of laundry detergents or cleaning agents that can advantageously be contained in the fluid reservoir or which can be contained in a laundry detergent or cleaner that contains fluid reservoirs according to the invention are described in more detail.

These ingredients include builders. Builders include, in particular, zeolites, silicates, carbonates, organic cobuilders and, if there are no ecological prejudices against their use, also the phosphates.

The applicable finely crystalline synthetic zeolite that contains bound water is preferably Zeolite A and/or P. Zeolite MAP® (commercial product of the Crosfield company) is especially preferred as Zeolite P. However, Zeolite X is also usable, as are mixtures of A, X and/or P. A co-crystallizate of Zeolite X and Zeolite A (ca. 80% by weight Zeolite X) sold by CONDEA Augusta S. p. A as VEGOBOND AX® is commercially available and preferred for use in the context of the present invention. It can be described by the formula $$n\mathrm{Na_2O.(1\text{-}}n\mathrm{)K_2O.Al_2O_3.(2\text{-}2.5)SiO_2.(3.5\text{-}5.5)H_2O}$$

The zeolite can also be as a powdering agent. Suitable zeolites have preferably have a mean particle size less than 10 μm (volume distribution; measuring method: Coulter Counter) and contain preferably 18 to 22% by weight, particularly 20 to 22% by weight bound water.

Suitable crystalline lamellar sodium silicates have the general formula $NaMSi_xO_{2x+1}.H_2O$, in which means sodium or hydrogen, x is a number from 1.9 to 4 and y is a number from 0 to 20, and preferred values for x are 2, 3 or 4. Preferred crystalline lamellar silicates having the formula stated are those in which M stands for sodium and x takes on the value of 2 or 3. In particular, both β- and δ-sodium disilicate, $Na_2Si_2O_5.yH_2O$, are preferred.

Crystalline lamellar silicates having the general formula $NaMSi_xO_{2x+1}.H_2O$, in which M represents sodium or hydrogen, x is a number from 1.9 to 22, preferably from 1.9 to 4, and y stands for a number from 0 to 33, can also be used particularly preferably. The crystalline lamellar silicates having the formula $NaMSi_xO_{2x+1}.yH_2O$ are, for example, sold by Clarian GmbH (Germany) under the trade name Na-SKS. Examples of these silicates include Na-SKS-1 ($Na_2Si_{22}O_{45}.xH_2O$, kenyaite), Na-SKS-2 ($Na_2Si_{14}O_{29}.xH_2O$ (magadite), Na-SKS-3 ($Na_2Si_8O_{17}.xH_2O$) or Na-SKS-4 ($Na_2Si_4O_9.xH_2O$, makatite).

Crystalline lamellar silicates having the formula $NaMSi_xO_{2x+1}.yH_2O$, in which x stands for 2, are also particularly suitable. The particularly suitable ones of these are Na-SKS-5 (α-$Na_2Si_2O_5$), Na-SKS-7 (β-$Na_2Si_2O_5$, natrosilite), Na-SKS-9 ($NaHSi_2O_5.H_2O$), Na-SKS-10 ($NaHSi_2O_5.3H_2O$, kanemite), Na-SKS-11 (t-$Na_2Si_2O_5$) and Na-SKS-13 ($NaHSi_2O_5$), but especially Na-SKS-6 (δ-$Na_2Si_2O_5$).

Amorphous sodium silicates having a $Na_2O:SiO_2$ ratio of 1:2 to 1:3.3, preferably 1:2 to 1:2.8 and particularly 1:2 to 1:2.6 which have delayed dissolution and exhibit secondary washing properties are also usable. The delay of dissolution compared with the usual sodium silicates can be accomplished in various ways, such as by surface treatment, compounding, compacting/compressing or by overdrying. In the context of this invention the term "amorphous" is understood to include "X-ray amorphous". This means that the silicates do not give sharp X-ray reflections in X-ray diffraction experiments, such as are typical of crystalline substances. Instead, they always exhibit one or more maxima of the scattered X-radiation indicating a range of several degrees for the angle of diffraction. However, if the silicate articles give diffuse or even sharp diffraction maxima in electron diffraction experiments, that can lead to very good or even particularly good builder characteristics. That can be interpreted to mean that the products have microcrystalline regions of the magnitude of 10 to a few hundred nm, with values up to a maximum of 50 nm and particularly up to a maximum of 20 nm preferred. Such so-called X-ray amorphous silicates likewise exhibit delayed dissolution in comparison with the usual water glasses. Compressed/compacted amorphous silicates, compounded amorphous silicates and over-dried X-ray amorphous silicates are particularly preferred.

In the context of the present invention it can be preferable for this/these silicate(s), preferably alkali silicates, especially preferably crystalline or amorphous alkali disilicates, to be contained in laundry detergents or cleaners in proportions of 10 to 60% by weight, preferably 15 to 50% by weight, and especially 20 to 40% by weight, based in each case on the weight of the laundry detergent or cleaner.

Obviously it is also possible to use the generally known phosphates as builder substances, as long as it is not necessary to avoid such use for ecological reasons. That is particularly the case for use of agents according to the invention as washing agents for dishwashing machines. Among the multitude of commercially available phosphates, the alkali metal phosphates are the most important for the laundry detergent and cleaner industry, with particular preference for pentasodium or pentapotassium triphosphate (sodium or potassium tripolyphosphate).

Alkali metal phosphate is the summary designation for the alkali metal (especially sodium and potassium) salts of the various phosphoric acids, in which one can distinguish metaphosphoric acids, $(HPO_3)_n$, and orthohosphoric acid, $H_3PO_4$, along with representatives of higher molecular weight. The phosphates combine several advantages: they act as alkali carriers, prevent lime deposition on machine parts or lime incrustations in cloth, and also contribute to the cleaning power.

Examples of suitable phosphates are sodium dihydrogen phosphate, $NaH_2PO_4$, in the form of the dihydrate (density 1.91 g/cm$^3$, melting point 60° C.) or in the form of the monohydrate (density 2.04 g/cm$^3$); disodium hydrogen phosphate (secondary sodium phosphate), $Na_2HPO_4$, which can be used anhydrous or with 2 moles of $H_2O$ (density 2.066 g/cm$^3$, water loss at 95° C.), 7 moles (density 1.68 g/cm$^3$, melting point 48° C. with loss of 5 $H_2O$) and 12 moles of water (density 1.52 g/cm$^3$, melting point 35° C. with loss of 5 $H_2O$), but particularly trisodium phosphate (tertiary sodium phosphate) $Na_3PO_4$, which can be used as the dodecahydrate, as the decahydrate (equivalent to 19-20% $P_2O_5$) or in the anhydrous form (equivalent to 39-40% $P_2O_5$).

Tripotassium phosphate (tertiary or tribasic potassium phosphate), $K_3PO_4$, is another preferred phosphate. Tetrasodium diphosphate (sodium pyrophosphate), $Na_4P_2O_7$ is also preferred. It exists in the anhydrous form (density 2.534 g/cm$^3$, melting point 988°, also reported as 880°) and as the decahydrate (density 1.815-1.836 g/cm$^3$, melting point 94° with loss of water). The corresponding potassium salt, potassium diphosphate (potassium pyrophosphate), $K_4P_2O_7$ is also preferred.

The industrially important pentasodium triphosphate, $Na_5P_3O_{10}$, is a non-hygroscopic colorless water-soluble salt that is anhydrous or crystallizes with 6 $H_2O$. It has the general formula Na—[P(O)ONa)—O]$_n$—Na with n=3. The corresponding potassium salt, pentapotassium triphosphate ($K_5P_3O_{10}$) (potassium tripolyphosphate) is commercially available as, for example, a 50% by weight solution (>23% $P_2O_5$, 25% $K_2O$). The potassium polyphosphates are widely used in the detergent or cleaning agent industry. Sodium potassium tripolyphosphates also exist. They are likewise usable in the context of the present invention. They are produced, for example, if sodium trimetaphosphate is hydrolyzed with KOH:

$$(NaPO_3)_3+2KOH \rightarrow Na_3K_2P_3O_{10}+H_2O$$

They can be used according to the invention exactly like sodium tripolyphosphate, potassium tripolyphosphate or mixtures of them. Mixtures of sodium tripolyphosphate and sodium potassium tripolyphosphate, or mixtures of potassium tripolyphosphate and sodium potassium tripolyphosphate, or mixtures of sodium tripolyphosphate and potassium tripolyphosphate and sodium potassium tripolyphosphate are also usable according to the invention.

If phosphates are used as washing or cleaning active substances in laundry detergents or cleaners in the context of the present invention, the preferred agents contain this/these phosphate(s), preferably alkali metal phosphates, especially preferably pentasodium or pentapotassium triphosphate (sodium or potassium tripolyphosphate) in proportions of 5 to 80% by weight, preferably 15 to 75% by weight, and especially 20 to 70% by weight, based in each case on the weight of the laundry detergent or cleaner.

It is preferable to use potassium tripolyphosphate and sodium tripolyphosphate, in particular, in a weight ratio of more than 1:1, preferably more than 2:1, preferably more than 5:1, especially preferably more than 10:1 and particularly more than 20:1. It is particularly preferable to use potassium tripolyphosphate alone without admixtures of other phosphates.

Alkali carriers are other builders. Alkali carriers include, for example, alkali metal hydroxides, alkali metal carbonates, alkali metal bicarbonates, alkali metal sesquicarbonates, the alkali silicate and alkali metasilicates mentioned, and mixtures of those substances. In the context of the present invention it is preferred to use the alkali carbonates, especially sodium carbonate, sodium bicarbonate, or sodium sesquicarbonate. A builder system comprising a mixture of tripolyphosphate and sodium carbonate is particularly preferred. A builder system comprising a mixture of tripolyphosphate and sodium carbonate and sodium disilicate is likewise particularly preferred.

The alkali metal hydroxides are used in low proportions if at all because of their poor chemical compatibility with the other ingredients of laundry detergents and cleaners, in comparison with other builders. They are preferably used in proportions of less than 10% by weight, preferably less than 6% by weight, especially preferably below 4% by weight, and particularly below 2% by weight, based in each case on the total weight of the laundry detergent or cleaner. Agents that contain less than 0.5%, based on their total weight, and especially no alkali metal hydroxides, are particularly preferred.

It can be especially preferable to use carbonate(s) and/or bicarbonate(s), preferably alkali carbonates, especially preferably sodium carbonate, in proportions of 2 to 50% by weight, preferably 5 to 40% by weight, and particularly 7.5 to 30% by weight, based in each case on the weight of the laundry detergent or cleaner. Agents that contain less than 20% by weight, preferably less than 17% by weight, preferably less than 13% by weight, and particularly less than 9% by weight, based in each case on the weight of the cleaner, of carbonate(s) and/or bicarbonate(s), preferably alkali carbonate(s), especially preferably sodium carbonate, can be particularly preferred.

Polycarboxylates/polycarboxylic acids, polymeric polycarboxylates, aspartic acid, polyacetals, dextrins, other organic cobuilders (see below) and phosphonates must be mentioned as organic cobuilders. These classes of materials are described in the following.

Examples of usable organic builders are the polycarboxylic acids, which can be used as their sodium salts. Here 'polycarboxylic acids' means those carboxylic acids that bear more than one acid function. Examples of those include citric acid, adipic acid, succinic acid, glutaric acid, malic acid, tartaric acid, maleic acid, fumaric acid, sugar acids, aminocarboxylic acids, and nitrilotriacetic acid (NTA) as long as their use in not objectionable for ecologic reasons, and mixtures of them. Preferred salts are the salts of the polycarboxylic acids such as citric acid, adipic acid, succinic acid, glutaric acid, tartaric acid, sugar acids, and mixtures of those.

The acids can also be used as such. The acids, aside from their builder action, typically also have the property of an acidifying component and so also serve to adjust a lower and milder pH of the laundry detergent or cleaner. In particular, citric acid, succinic acid, glutaric acid, adipic acid, gluconic acid, and arbitrary mixtures of them must be named.

Polymeric polycarboxylates are further suitable as builders. They include, for example, the alkali metal salts of polyacrylic acid or polymethacrylic acid, for instance, those with relative molecular weights of 500 to 70,000 g/mol.

The molecular weights stated for polymeric polycarboxylates are, in the sense of this document, weight-average molecular weights, $M_w$, of the particular acid form. They are basically determined by means of gel permeation chromatography (GPC) using a UV detector. The measurement is made versus an external polyacrylic acid standard, which gives realistic molecular weights because of its structural relation with the polymers being examined. These figures clearly diverge from the molecular weight data found when polystyrenesulfonic acids are used as standards. The molecular weights measured with polystyrenesulfonic acids are generally distinctly higher than those reported in this document.

Polyacrylates preferably having molecular weights of 2,000 to 20,000 are especially suitable polymers. Again, the short-chain polyacrylates of this group, having molecular weights of 2,000 to 10,000 are preferred, and those with molecular weights of 3,000 to 5,000 are particularly preferred of this group because of their superior solubility.

Copolymeric polycarboxylates are further suitable, especially those that are copolymers of acrylic acid with methacrylic acid and of acrylic acid or methacrylic acid with maleic acid. The copolymers of acrylic acid with maleic acid that contain 50 to 90% by weight acrylic acid and 50 to 10% by weight maleic acid have proven particularly suitable. Their relative molecular weights, based on the free acids, are generally 2,000 to 70,000 g/mol, preferably 20,000 to 50,000 g/mol, preferably 20,000 to 50,000 g/mol, and particularly 30,000 to 40,000 g/mol.

The (co)polymeric polycarboxylates can be used either as the powder or as the aqueous solution. Laundry detergents or cleaners contain preferably 0.5 to 20% by weight optionally (co)polymeric polycarboxylates, and especially 3 to 10% by weight.

The polymers can also contain allylsulfonic acids, such as allyloxybenzensulfonic acid and methallylsulfonic acid as monomers to improve the water solubility.

Biodegradable polymers made up of more than two different monomer units are particularly preferred, such as those that contain as monomers salts of acrylic acid and maleic acid as well as vinyl alcohol or vinyl alcohol derivatives, or which contain as monomers salts of acrylic acid and 2-alkylallylsulfonic acid as well as sugar derivatives.

Other preferred copolymers are those that contain as monomers preferably acrolein and acrylic acid/acrylic acid salts or acrolein and vinyl acetate.

Likewise, polymeric aminodicarboxylic acids, their salts, or their precursors must be mentioned as other preferred builder substances. Polyaspartic acids or their salts are especially preferred.

Polyacetals, which can be obtained by reaction of dialdehydes with polyol carboxylic acids having 5 to 7 C atoms and at least 3 hydroxyl groups are other suitable builder substances. Preferred polyacetals are obtained from dialdehydes such as glyoxylate, glutaraldehyde and terephthaldehyde or mixtures of them and from polyol carboxylic acids such as gluconic acid and/or gluconoheptanoic acid.

Dextrins, such as oligomers or polymers of carbohydrates, which can be obtained by partial hydrolysis of starches, are other suitable organic builder substances. The hydrolysis can be done by the usual processes, such as acid-catalyzed or enzyme-catalyzed processes. They are preferably hydrolysis products with mean molecular weights in the range of 400 to 500,000 g/mol. A polysaccharide having a dextrose equivalent (DE) in the range of 0.5 to 40, and especially 2 to 30, is preferred. DE is a useful measure of the reducing action of a polysaccharide in comparison with dextrose, which has a DE of 100.

Both maltodextrins with a DE between 3 and 20; and dry glucose syrups with DEs between 20 and 37 are usable, as are the so-called yellow dextrins and white dextrins with higher molecular weights in the range of 2,000 to 30,000 g/mol.

The oxidized derivatives of such dextrins are products of their reaction with oxidizing agents which are able to oxidize at least one alcohol function of the saccharide ring to the carboxylic acid function.

Oxydisuccinates and other derivatives of disuccinates, preferably ethylenediamine disuccinate are other suitable cobuilders. It is preferable to use ethylenediamine-N,N'-disuccinate (EDDS) in the form of its sodium or magnesium salt. Glycerol disuccinate and glycerol trisuccinate are also preferred in this respect. Suitable proportions for use in formulations containing zeolite and/or silicate can, for example, be 3 to 15% by weight.

Examples of other usable organic cobuilders are acetylated hydroxycarboxylic acids or their salts, which can optionally be in the lactone form and which have at least 4 carbon atoms and at least one hydroxyl group as well as not more than two acid groups.

Furthermore, all the compounds that can form complexes with alkaline earth cations can be used as builders.

The group of surfactants includes the nonionic, anionic, cationic and amphoteric surfactants.

All the nonionic surfactants known to those skilled in the art can be used as the nonionic surfactants. Low-foaming nonionic surfactants can be used as preferred nonionic surfactants, for instance. It is particularly preferable for the laundry detergent or cleaner to contain nonionic surfactants from the group of alkoxylated alcohols. It is preferable to use as nonionic surfactants alkoxylated, advantageously ethoxylated, particularly primary alcohols having preferably 8 to 18 C atoms and an average of 1 to 12 moles of ethylene oxide (EO) per mole of alcohol. The alcohol group can be linear or, preferably, methyl-branched in the 2 position, or it can contain a mixture of linear and methyl-branched groups, such as those that commonly occur in oxoalcohol groups. In particular, though, alcohol ethoxylates having linear groups of alcohols of natural origin having 12 to 18 C atoms, such as those from coco, palm, tallow, or oleyl alcohol, and an average of 2 to 8 moles of EO per mole of alcohol are preferred. The preferred ethoxylated alcohols include, for example, $C_{12}$-$C_{14}$ alcohols with 3 EO or 4 EO, $C_{9-11}$ alcohols having 7 EO, $C_{13-15}$ alcohols having 3 EO, 5 EO, 7 EO or 8 EO, $C_{12-18}$ alcohols having 3 EO, 5 EO or 7 EO, and mixtures of those, such as mixtures of $C_{12-14}$ alcohols with 3 EO and $C_{12-18}$ alcohol with 5 EO. The degrees of ethoxylation stated are statistical averages, which can be an integer or fraction for a particular product. Preferred alcohol ethoxylates exhibit a narrowed homolog distribution (narrow-range ethoxylates, NRE). In addition to these nonionic surfactants, fatty alcohols having more than 12 EO can also be used. Examples of those are tallow alcohols having 14 EO, 25 EO, 30 EO or 40 EO.

One can also use alkyl glycosides of the general formula $RO(G)_x$, in which R is a primary straight-chain or methyl-branched aliphatic group, especially one methyl-branched in the 2 position, having 8 to 22, preferably 12 to 18 C atoms, and G is the symbol for a glycose unit having 5 or 6 C atoms, preferably glucose. The degree of oligomerization, x, which indicates the distribution of monoglycosides and oligoglycosides, is an arbitrary number between 1 and 10. It is preferable for x to be 1.2 to 1.4.

Another class of preferably usable nonionic surfactants that can be used either as the only nonionic surfactant or in combination with other nonionic surfactants, is that of the alkoxylated, preferably ethoxylated or ethoxylated and propoxylated fatty acid alkyl esters, preferably having 1 to4 carbon atoms in the alky chains.

Nonionic surfactants of the amine oxide type, such as N-cocoalkyl-N,N-dimethylamine oxide and N-tallowalkyl-N,N-dihydroxyethylamine oxide; and the fatty acid alkanolamides, can also be suitable. The proportion of these nonionic surfactants preferably does not exceed that of the ethoxylated fatty alcohols, and is particularly not more than half of that.

Polyhydroxyfatty acid amides having the formula

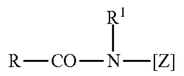

in which R stands for an aliphatic acyl group having 6 to 22 carbon atoms, $R^1$ stands for hydrogen, or an alkyl or hydroxyalkyl group with 1 to 4 carbon atoms, and [Z] stands for a linear or branched polyhydroxyalkyl group with 3 to 10 carbon atoms and 3 to 10 hydroxyl groups are also preferred surfactants. The poyhydroxyfatty acid amides are known substances that can normally be obtained by reductive amination of a reducing sugar with ammonia, an alkylamine or an alkanolamine, then subsequent acylation with a fatty acid, a fatty acid alkyl ester or a fatty acid chloride.

The group of polyhydroxyfatty acid amides also includes compounds of the formula

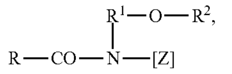

in which the R stands for a linear or branched alkyl or alkenyl group having 7 to 12 carbon atoms, $R^1$ stands for a linear, branched or cyclic alkyl group or an aryl group having 2 to 18 carbon atoms and $R^2$ stands for a linear, branched or cyclic alkyl group or an aryl group or an oxyalkyl group having 1 to 8 carbon atoms, with $C_{1-4}$-alkyl or phenyl groups preferred, and [Z] stands for a linear polyhydroxyalkyl group, the alkyl chain of which is substituted with at least two hydroxyl groups, or alkoxylated, preferably ethoxylated or propoxylated derivatives of these groups.

[Z] is preferably obtained by reductive amination of a reducing sugar, such as glucose, fructose, maltose, lactose, galactose, mannose or xylose. The N-alkoxy- or N-aryloxy-substituted compounds can, for example, be converted into the desired polyhydroxy fatty acid amides by reaction with fatty acid methyl esters in the presence of an alkoxide as the catalyst.

Surfactants containing one or more tallow alcohols having 20 to 30 EO in combination with a silicone antifoam can be used with particular preference.

Nonionic surfactants of the group of the alkoxylated alcohols, particularly preferably from the group of mixed alkoxylated alcohols and especially from the group of EO-AO-0EO nonionic surfactants are likewise used with special preference.

Nonionic surfactants having melting points above room temperature are particularly preferred. Nonionic surfactant(s) having (a) melting point(s) above 20° C., preferably above 25° C., especially preferably between 25 and 60° C., and particularly between 26.6 and 43.3° C. is/are particularly preferred.

Low-foaming nonionic surfactants that can be solid or highly viscous at room temperature, having softening or melting points in the stated temperature range, are suitable nonionic surfactants. If nonionic surfactants that are highly viscous at room temperature are used, it is preferable for them to have a viscosity above 20 Pa·s, preferably above 35 Pa·s, and particularly above 40 Pa·s. Surfactants having a waxy consistency at room temperature are also preferred.

Surfactants used preferably, that are solid are room temperature, are derived from the groups of alkoxylated nonionic surfactants, especially the ethoxylated primary alcohols and mixtures of these surfactants having more complex structure, such as polyoxypropylene/polyoxyethylene/polyoxypropylene ((PO/EO/PO) nonionic surfactants). Such ((PO/EO/PO) nonionic surfactants are further distinguished by good foam control.

In a preferred embodiment of the present invention, the nonionic surfactant having a melting point above room temperature is an ethoxylated nonionic surfactant obtained from the reaction of a monohydroxyalkanol or alkylphenol having 6 to 20 C atoms with preferably at least 12 moles, especially preferably at least 15 moles, and particularly at least 20 moles of ethylene oxide per mole of alcohol or alkylphenol.

A particularly preferred nonionic surfactant that is solid at room temperature is obtained from a straight-chain fatty alcohol having 16 to 20 carbon atoms ($C_{16-20}$ alcohol), preferably a $C_{18}$ alcohol, and at least 12 moles, preferably at least 15 moles, and especially at least 20 moles of ethylene oxide. Of these, the so-called "narrow range ethoxylates" (see above) are especially preferred.

Ethoxylated nonionic surfactants obtained from $C_{6-20}$ monohydroxyalkanols or $C_{6-20}$ alkylphenols or $C_{18-20}$ fatty alcohols and more than 12 moles, preferably more than 15 moles, and especially more than 20 moles of ethylene oxide per mole of alcohol are used with special preference.

It is preferable for the nonionic surfactant that is solid at room temperature also to have propylene oxide units in the molecule. Preferably such PO units make up as much as 25% by weight, especially preferably up to 20% by weight, and particularly up to 15% by weight of the total molecular weight of the nonionic surfactant. Especially preferred nonionic surfactants are ethoxylated monohydroxyalkanols or alkylphenols that also have polyoxyethylene-polyoxypropylene block copolymer units. The alcohol or alkylphenol portion of such nonionic surfactant molecules preferably amounts to more than 30% by weight, especially preferably more than 50% by weight, and particularly more than 70% by weight of the total molecular weights of such nonionic surfactants. Preferred agents are distinguished by containing ethoxylated and propoxylated nonionic surfactants in which the propylene oxide units in the molecule amount to as much as 25% by weight, preferably 20% by weight, and particularly 15% by weight of the total molecular weight of the nonionic surfactant:

Other nonionic surfactants that can be used with particular preference, having melting points above room temperature, contain 40 to 70% of a polyoxypropylene/polyoxyethylene/polyoxypropylene block polymer blend that contains 75% by weight of an inverse block copolymer of polyoxyethylene and polyoxypropylene with 17 moles of ethylene oxide and 44 moles of propylene oxide, and 25% % by weight of a block copolymer of polyoxyethylene and polyoxypropylene, initiated with trimethylolpropane and containing 24 moles of ethylene oxide and 99 moles of propylene oxide per mole of trimethylolpropane.

Nonionic surfactants that can be used with special preference are, for example, obtainable from Olin Chemicals under the name Poly Tergent® SLF-18.

Surfactants having the formula $$R^1O[CH_2CH(CH_3)O]_x[CH_2CH_2O]_yCH_2CH(OH)R^2,$$

in which $R^1$ stands for a linear or branched aliphatic hydrocarbon group having 4 to 18 carbon atoms, or mixtures of them, $R^2$ stands for a linear or branched hydrocarbon group having 2 to 26 carbon atoms, or mixtures of them, and x stands for values between 0.5 and 1.5, and y stands for a value of at least 15, are other specially preferred nonionic surfactants.

Other nonionic surfactants that can be used preferably are the end-group-capped poly(oxyalkylated) nonionic surfactants having the formula $$R^1O[CH_2CH(R^3)O]_x[CH_2]_kCH(OH)[CH_2]_jOR^2,$$

in which $R^1$ and $R^2$ stand for linear or branched, saturated or unsaturated aliphatic or aromatic hydrocarbon groups with 1 to 30 carbon atoms, $R^3$ stands for H or a methyl, ethyl, n-propyl, isopropyl, n-butyl, 2-butyl, or 2-methyl-2-butyl group, x stands for values between 1 and 30, and k and j stand for values between 1 and 12, preferably between 1 and 5. If x≧2, each $R^3$ on the preceding formula $$R^1O[CH_2CH(R^3)O]_x[CH_2]_kCH(OH)[CH_2]_jOR^2,$$

can be different. $R^1$ and $R^2$ are preferably linear or branched, saturated or unsaturated, aliphatic or aromatic hydrocarbon groups having 6 to 22 carbon atoms, with groups having 8 to 18 C atoms being especially preferred. H, —$CH_3$ or —$CH_2CH_3$ are especially preferred for the group $R^3$. Especially preferred values of x are in the range of 1 to 20, preferably 6 to 15.

As described above, each $R^3$ in the preceding formula can be different if x≧2. In this way, the alkylene oxide unit in the square brackets can be varied. For example, if x stands for 3, the group $R^3$ can be selected to make up ethylene oxide ($R^3$=H) or propylene oxide ($R^3$=—$CH_3$) units. They can follow each other in any sequence, such as (EO)(PO)(EO), (EO)(EO)(PO), (EO)(EO)(EO), (PO)(EO)(PO), (PO)(PO)(EO) and (PO)(PO)(PO). Here the value of x was selected to be 3, and can be larger, with the the range of variation increasing with rising x values and, for example, a large number of (EO) groups combined with a small number of (PO) groups, or conversely.

Particularly preferred end-group-capped poly(oxyalkylated) alcohols of the preceding formula have values of k=1 and j=1, so that the preceding formula simplifies to $$R^1O[CH_2CH(R^3)O]_xCH_2CH(OH)CH_2OR^2$$

In the latter formula, $R^1$, $R^2$, and $R^3$ are defined as above, and x stands for numbers from 1 to 30, preferably from 1 to 20 and particularly from 6 to 18. Surfactants in which the groups $R^1$ and $R^2$ have 9 to 14 C atoms, $R^3$ stands for H and x has values of 6 to 15 are particularly referred.

If one combines the latter statements, end-group-capped poly(oxyalkylated) nonionic surfactants having the formula $$R^1O[CH_2CH(R^3)O]_x[CH_2]_kCH(OH)[CH_2]_jOR^2,$$

in which $R^1$ and $R^2$ stand for linear or branched, saturated or unsaturated, aliphatic or aromatic hydrocarbon groups having 1 to 30 carbon atoms, $R^3$ stands for H or for a methyl, ethyl, n-propyl, isopropyl, n-butyl, 2-butyl, or 2-methyl-2-butyl group, x stands for values between 1 and 30, and k and j stand for values between 1 and 12, preferably between 1 and 5 are preferred. Surfactants of the type $$R^1O[CH_2CH(R^3)O]_xCH_2CH(OH)CH_2OR^2,$$

in which x stands for numbers from 1 to 30, preferably from 1 to 20 and particularly from 6 to 18, are particularly preferred.

Low-foaming nonionic surfactants having alternating ethylene oxide and alkylene oxide units have proven to be particularly preferred in the context of the present invention. Of these, again, surfactants with EO-AO-EO-AO blocks are preferred, with one to ten EO or AO groups in each block being joined together before a block from the other group follows. Here, nonionic surfactants having the general formula $$R^1—O—(CH_2—CH_2—O)_w—(CH_2—\underset{R^2}{\underset{|}{CH}}—O)_x—(CH_2—CH_2—O)_y—(CH_2—\underset{R^3}{\underset{|}{CH}}—O)_z—H$$

are preferred, with $R^1$ standing for a straight or branched, saturated or singly or multiply unsaturated $C_{6-24}$ alkyl or alkenyl group; each group $R^2$ or $R^3$, independently of each other, is selected from —$CH_3$, —$CH_2$—$CH_3$, —$CH_2CH_2$—$CH_3$, $CH(CH_3)_2$, and the indices w, x, y and z, independently of each other, stand for integers from 1 to 6.

The preferred nonionic surfactants having the formula above can be produced from the corresponding alcohols, $R^1$—OH and ethylene oxide or alkylene oxide. The group $R^1$ in the formula above can vary, depending on the source of the alcohol. If natural sources are used, the group $R^1$ has an even number of carbon atoms and is generally unbranched. The linear groups from alcohols of natural origin with 12 to 18 C atoms, such as from coconut, palm, tallow, or oleyl alcohol, are preferred. Examples of alcohols accessible from synthetic sources are the Guerbet alcohols or groups methyl-branched at the 2 position, or mixtures of linear and methyl-branched groups, such as usually occur in oxoalcohol groups. Independently of the manner of production of the alcohols used in the nonionic surfactants optionally contained in the agents, those nonionic surfactants are preferred in which $R^1$ in the formula above stands for an alkyl group having 6 to 24, preferably 8 to 20, especially preferably 9 to 15 and particularly 9 to 11 carbon atoms.

Butylene oxide, along with propylene oxide, is an alkylene oxide unit that can be contained in the preferred nonionic surfactants as an alternate to the ethylene oxide unit. However, even other alkylene oxides, in which $R^2$ or $R^3$, independently of each other, are selected from —$CH_2CH_2CH_3$ or —$CH(CH_3)_2$ are suitable. Preferred nonionic surfactants are those of the formula above in which $R^2$ or $R^3$ stands for a group —$CH_3$, w and x, independently of each other, stand for values of 3 or 4, and y and z, independently of each other; stand for values of 1 or 2.

In summary, those nonionic surfactants are particularly preferred that have a $C_{9-15}$-alkyl group with 1 to 4 ethylene oxide units, followed by 1 to 4 propylene oxide units, followed by 1 to 4 ethylene oxide units, followed by 1 to 4 propylene oxide units. Those surfactants have the required low viscosity in aqueous solution and can be used with special preference according to the invention.

Other preferred nonionic surfactants are the end-group-capped poly(oxyalkylated) nonionic surfactants having the formula $$R^1O[CH_2CH(R^3)O]_xCH_2,$$

in which $R^1$ stands for linear or branched, saturated or unsaturated, aliphatic or aromatic hydrocarbon groups with 1 to 30 carbon atoms, $R^2$ stands for linear or branched, saturated or unsaturated, aliphatic or aromatic hydrocarbon groups with 1 to 30 carbon atoms, preferably having between 1 and 5 hydroxyl groups and preferably further functionalized with an ether group, $R^3$ stands for H or a methyl, ethyl, n-propyl, iso-propyl, n-butyl or 2-methyl-2-butyl group, and x stands for values between 1 and 40.

In a particularly preferred embodiment of the present application, $R^3$ in the general formula above stands for H. Of the resulting group of end-group-capped poly(oxyalkylated) nonionic surfactants of the formula $$R^1O[CH_2CH_2O]_xR^2$$

those nonionic surfactants are particularly preferred in which $R^1$ stands for a linear or branched, saturated or unsaturated, aliphatic or aromatic having 1 to 30 carbon atoms, preferably having 4 to 20 carbon atoms; $R^2$ stands for linear or branched, saturated or unsaturated, aliphatic or aromatic hydrocarbon groups having 1 to 30-carbon atoms, preferably having between 1 and 5 hydroxyl groups, and x stands for values between 1 and 40.

In particular, those end-group-capped poly(oxyalkylated) nonionic surfactants are preferred that, according to the formula $$R^1O[CH_2CH_2O]_xCH_2CH(OH)R^2$$

have, aside from a group $R^1$, which stands for linear or branched, saturated or unsaturated, aliphatic or aromatic hydrocarbon groups with 1 to 30 carbon atoms, preferably with 4 to 20 carbon atoms, also have a linear or branched, saturated or unsaturated, aliphatic or aromatic hydrocarbon group $R^2$ with 1 to 30 carbon atoms, which is adjacent to a monohydroxylated intermediate group —$CH_2CH(OH)$—. In this formula, x stands for values between 1 and 90.

Nonionic surfactants having the general formula $$R^1O[CH_2CH_2O]_xCH_2CH(OH)R^2,$$

are especially preferred, in which there is, aside from a group $R^1$, which stands for linear or branched, saturated or unsaturated, aliphatic or aromatic hydrocarbon groups with 1 to 30 carbon atoms, preferably with 4 to 22 carbon atoms, also a linear or branched, saturated or unsaturated, aliphatic or aromatic hydrocarbon group $R^2$ with 1 to 30 carbon atoms, preferably 2 to 22 carbon atoms, which is adjacent to a monohydroxylated intermediate group —$CH_2CH(OH)$— and in which x stands for values between 40 and 80, preferably for values between 40 and 60.

The corresponding end-group-capped poly(oxyalkylated) nonionic surfactants having the formula above can be obtained, for instance, by reacting a terminal epoxide having the formula $R^2CH(O)CH_2$ with an ethoxylated alcohol having the formula $R^1O[CH_2CH_2O]—_{x-1}CH_2CH_2OH$.

Especially preferred are those end-group-capped poly (oxyalkylated) nonionic surfactants having the formula $$R^1O[CH_2CH_2O]_x[CH_2CH(CH_3)O]_yCH_2CH(OH)R^2,$$

in which $R^1$ and $R^2$, independently of each other, stand for a linear or branched, saturated or singly or multiply unsaturated, hydrocarbon group having 2 to 26 carbon atoms, $R^3$, independently of each other, is selected from —$CH_3$, —$CH_2CH_3$, —$CH_2CH_2$—$CH_3$, or —$CH(CH_3)_2$, but with —$CH_3$ preferred, and x and y, independently of each other, stand for values between 1 and 32, with nonionic surfactants in which the values of x are from 15 to 32 and the values of y are 0.5 and 1.5 quite particularly preferred.

Surfactants having the general formula $$R^1—O—[CH_2—CH_2—O]_x—[CH_2—\underset{R^3}{\underset{|}{CH}}—O]_y—CH_2—CH(OH)R^2,$$

in which $R^1$ and $R^2$, independently of each other, stand for a linear or branched, saturated or multiply unsaturated, hydrocarbon group having 2 to 26 carbon atoms, $R^3$, independently of each other, is selected from —$CH_3$, —$CH_2CH_3$, —$CH_2CH_2$—$CH_3$, or $CH(CH_3)_2$, but with —$CH_3$ preferred, and x and y independently of each other stand for values between 1 and 32, with nonionic surfactants having values of x of 15 to 32 and of y of 0.5 and 1.5 are quite particularly preferred.

The carbon chain lengths stated, as well as the degrees of ethoxylation or alkoxylation for the preceding nonionic surfactants are statistical averages, which can be integers or fractions for a particular product. Because of the production process, commercial products of the formulas stated generally are not made up of individual representatives, but of mixtures, so that there can be fractional numbers for both the carbon chain lengths and for the degrees of ethoxylation or alkoxylation.

Obviously, the nonionic surfactants named above can be used not only as individual substances but also as surfactant mixtures of two, three, four or more surfactants. Surfactant mixtures are not considered mixtures of nonionic surfactants which in their totality fall in one of the general formulas given above, but rather mixtures containing two, three, four or more nonionic surfactants that can be described by different ones of the general formulas presented above.

As anionic surfactants, those of the sulfonate and sulfate type are used. The preferred surfactants of the sulfonate type are $C_{9-13}$-alkylbenzene-sulfonates, olefin sulfonates, i. e., mixtures of alkene and hydroxyalkane sulfonates, and disulfonates, such as are obtained, for example, from $C_{12-18}$-monoolefins with terminal or internal double bonding by sulfonation with gaseous sulfur trioxide and subsequent acidic or alkaline hydrolysis of the sulfonation products. Alkane sulfonates, obtained from $C_{12-18}$-alkanes, for instance, by sulfochlorination or sulfoxidation with subsequent hydrolysis or neutralization, are also suitable. Esters of α-sulfofatty acids (ester sulfonates), such as the α-sulfonated methyl esters of hydrogenated coco, palm kernel or tallow fatty acids, are also suitable.

Sulfonated fatty acid glycerol esters are other suitable anionic surfactants. Fatty acid glycerol esters are understood to be the mono, di and tri-esters, and mixtures of them, such as are obtained on production by esterification of a monoglycerol with 1 to 3 moles of fatty acid, or transesterification of triglycerides with 0.3 to 2 moles of glycerol. Preferred sulfonated fatty acid glycerol esters are sulfonation products of saturated fatty acids having 6 to 22 carbon atoms, such as caproic acid, caprylic acid, capric acid, myristic acid, lauric acid, palmitic acid, stearic acid or behenic acid.

Preferred alk(en)yl sulfates are the alkali, and especially the sodium salts of the sulfuric acid hemiesters of the $C_{12}$-$C_{18}$ fatty alcohols, for example, of coco fatty alcohol, tallow fatty alcohol, lauryl, myristyl, cetyl or stearyl alcohol or of the $C_{10}$-$C_{20}$ oxoalcohols and the hemiesters of secondary alcohols having those chain lengths. Alk(en)yl sulfates of the specified chain lengths which comprise a synthetically produced straight chain petrochemically based alkyl group, which have degradative behavior similar to the adequate compounds based on fatty chemical raw materials are also preferred. The $C_{12}$-$C_{16}$-alkyl sulfates, $C_{12}$-$C_{15}$-alkyl sulfates, and $C_{14}$-$C_{15}$-alkyl sulfates are preferred from the viewpoint of detergent technology. 2,3-alkyl sulfates, which can be obtained from Shell Oil Company under the DAN® name are also suitable anionic surfactants.

The sulfuric acid hemiesters of straight-chain or branched $C_{7-21}$ alcohols ethoxylated with 1 to 6 moles of ethylene oxide are also suitable, such as 2-methyl branched $C_{9-11}$-alcohols with an average of 3.5 moles of ethylene oxide (EO) or $C_{12-18}$ fatty alcohols with 1 to 4 EO.

The salts of the alkyl sulfosuccinic acids are other suitable anionic surfactants. They are also called sulfosuccinates or sulfosuccinic acid esters, and are hemiesters or diesters of sulfosuccinic acid with alcohols, preferably fatty alcohols and particularly ethoxylated fatty alcohols. Preferred sulfosuccinates comprise $C_{8-18}$ fatty alcohol groups or mixtures of them. Particularly preferred sulfosuccinates comprise a fatty alcohol group derived from ethoxylated fatty alcohols which are themselves considered nonionic surfactants. Again, sulfosuccinates, the fatty alcohol groups of which are derived from ethoxylated fatty alcohols with limited homolog distribution are particularly preferred. Likewise, it is also possible to use alk(en)ylsuccinic acids with preferably 8 to 18 carbon atoms, or their salts, in the alk(en)yl chain.

Soaps, in particular, can be considered as other anionic surfactants. Soaps of saturated fatty acids, such as the salts of lauric acid, myristic acid, palmitic acid, stearic acid, hydrogenated erucic acid and behenic acid, as well as soap mixtures derived particularly from natural fatty acids, such as coco, palm kernel or tallow fatty acids, are suitable.

The anionic surfactants, including the soaps, can be in the form of their sodium, potassium or ammonium salts, as well as soluble salts of organic bases such as mono-, di- or triethanolamine. The anionic surfactants are preferably in the form of their sodium or potassium salts, and particularly the sodium salts.

The proportion of anionic surfactant in laundry detergents or cleaners can, for example, be in the range of 1-60% by weight, advantageously 5-40% by weight, and particularly 10-30% by weight.

Cationic surfactants and/or amphoteric surfactants can also be used in place of the specified surfactants or in combination with them.

Cationic compounds of the following formulas, for example, can be used as cationically active substances:

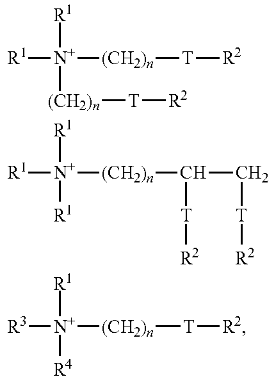

in which each $R^1$ group is selected, independently of each other, from $C_{1-6}$-alkyl, alkenyl or hydroxyalkyl groups; each $R^2$ group is selected, independently of each other, from $C_{8-28}$-alkyl or alkenyl groups; $R^3$=$R^1$ or $(CH_2)_n$T-$R^2$; $R^4$=$R^1$ or $R^2$ or $(CH_2)_n$-T-$R^2$; T=—$CH_2$—, —O—CO— or —CO—O—, and n is an integer from 0 to 5.

The proportion of cationic and/or amphoteric surfactants can preferably be less than 10% by weight, preferably less than 5% by weight, quite particularly preferably less than 2% by weight and particularly less than 1% by weight. It can also be preferable that no cationic or amphoteric surfactants are contained.

The group of polymers includes in particular the polymers with laundry detergent or cleaning action, such as the polymers that act as water softeners. In general, cationic, anionic and amphoteric polymers are usable along with nonionic polymers in laundry detergents or cleaners.

"Cationic polymers" in the sense of the present invention are polymers bearing a positive charge in the polymer molecule. That can be accomplished, for example, by (alkyl)-ammonium groups or other positively charged groups in the polymer chain. Particularly preferred cationic polymers are derived from the groups of quaternized cellulose derivatives, polysiloxanes with quaternary groups, cationic guar derivatives, polymeric dimethyldiallylammonium salts, and their copolymers with esters and amides of acrylic acid and methacrylic acid, copolymers of vinylpyrrolidone with quaternized derivatives of dialkylamino-acrylate and -methacrylate, vinylpyrrolidone-methylimidazolinium chloride copolymers, quaternized polyvinyl alcohols or the polymers with INCI names Polyquaternium 2, Polyquaternium 7, Polyquaternium 18 and Polyquaternium 27.

"Amphoteric polymers" in the sense of the present invention have also negatively charged groups or monomer units in the polymer chain, along with a positively charged group. These groups can, for example, be carboxylic acids, sulfonic acids, or phosphoric acids.

Preferred laundry detergents or cleaning agents are characterized by comprising a polymer having monomer units with the formula $R^1R^2C$=$CR^3R^4$, in which each group $R^1$, $R^2$, $R^3$, $R^4$, is selected, independently of each other, from hydrogen, derivatized hydroxyl group, $C_{1-30}$ linear or branched alkyl groups, aryl, aryl-substituted $C_{1-30}$ linear or branched alkyl groups, polyalkoxylated alkyl groups, heteroatomic organic groups having at least one positive charge without charged nitrogen, at least one quaternized N atom or at least one amino group having a positive charge in the pH sub-range of 2 to 11, or salts of them, provided that at least one group $R^1$, $R^2$, $R^3$, $R^4$ is a heteroatomic organic group having at least one positive charge without charged nitrogen, at least one quaternized N atom or at least one amino group with a positive charge.

In the context of the present invention, specially preferred cationic or amphoteric polymers contain as the monomer unit a compound having the general formula

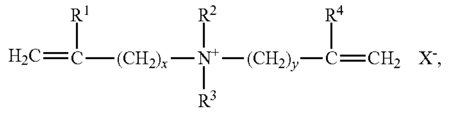

in which $R^1$ and $R^4$ independently of each other stand for H or for a linear or branched hydrocarbon group having 1 to 6 carbon atoms; $R^2$ and $R^3$, independently of each other, stand for an alkyl, hydroxylalkyl, or aminoalkyl group in which the alkyl group is linear or branched and has between 1 and 6 carbon atoms, and which is preferably a methyl group; x and y, independently of each other, stand for integers between 1 and 3. $X^-$ represents a counterion, preferably a counterion from the group of chloride, bromide, iodide, sulfate, bisulfate, methosulfate, lauryl sulfate, dodecylbenzenesulfonate, p-toluenesulfonate(tosylate), cumenesulfonate, xylenesulfonate, phosphate, citrate, formate, acetate or mixtures of them.

Preferred $R^1$ and $R^4$ groups in the formula above are selected from $-CH_3$, $-CH_2CH_3$, $-CH_2CH_2CH_3$, $-CH(CH_3)-CH_3$, $-CH_2OH$, $-CH_2CH_2OH$, $-CH(OH)-CH_3$, $CH_2-CH_2-CH_2-OH$, $-CH_2-CH(OH)-CH_3$, $-CH(OH)-CH_2-CH_3$ and $-CH_2-CH_2-O)_nH$.

Polymers having a cationic monomer unit of the general formula above in which $R^1$ and $R^4$ stand for H, $R^2$ and $R^3$ stand for methyl, and x and y are each 1 are quite specially preferred. The corresponding monomer unit having the formula $$H_2C{=}CH-(CH_2)-N^+(CH_3)_2-(CH_2)-CH{=}CH_2 \quad X^-$$

is also known as DADMAC (diallyldimethylammonium chloride) if X=chloride.

Other specially preferred cationic or amphoteric polymers comprise a monomer unit having the general formula $$R^1HC{=}CR^2-C(O)-NH-(CH_2)_x-N^+R^3R^4R^5, \quad X^-$$

in which the $R^1$, $R^2$, $R^3$, $R^4$, and $R^5$, independently of each other, stand for a linear or branched saturated or unsaturated alkyl or hydroxyalkyl group having 1 to 6 carbon atoms, preferably for a linear or branched alkyl group selected from $-CH_3$, $-CH_2CH_3$, $-CH_2CH_2CH_3$, $-CH(CH_3)-CH_3$, $-CH_2OH$, $-CH_2CH_2OH$, $-CH(OH)-CH_3$, $-CH_2-CH_2-CH_2-OH$, $-CH_2-CH(OH)-CH_3$, $-CH(OH)-CH_2-CH_3$ and $-(CH_2-CH_2-O)_nH$ and x stands for an integer between 1 and 6.

In the context of the present invention, those polymers having a cationic monomer unit of the general formula above in which $R^1$ stands for H and $R^2$, $R^3$, $R^4$, and $R^5$ stand for methyl, and x stands for 3, are quite specially preferred. The corresponding monomer units having the formula $$H_2C{=}C(CH_3)-C(O)-NH-(CH_2)_x-N^+(CH_3)_3 \quad X^-$$

are also called MAPTAC (methylacrylamidopropyl-trimethylammonium chloride) if $X^-$=chloride.

Polymers that comprise as monomer units diallyldimethylammonium salts and/or acrylamidopropyltrimethylammonium salts are preferred according to the invention.

The amphoteric polymers mentioned previously have not only cationic groups but also anionic groups or monomer units. Such anionic monomer units are derived, for instance, from the group of linear or branched saturated or unsaturated carboxylates, the linear or branched, saturated or unsaturated phosphonates, the linear or branched, saturated or unsaturated sulfates, or the linear or branched, saturated or unsaturated sulfonates. Preferred monomer units are acrylic acid, (meth)acrylic acid, dimethylacrylic acid, ethylacrylic acid, cyanoacrylic acid, vinylacetic acid, allylacetic acid, crotonic acid, maleic acid, fumaric acid, cinnamic acid and its derivatives, the allylsulfonic acids such as allyloxybenzenesulfonic acid and methallylsulfonic acids or the allylphosphonic acids.

Preferred usable amphoteric polymers are derived from the groups of the alkylacrylamide/acrylic acid copolymers, the alkylacrylamide/methacrylic acid copolymers, the alkylacrylamide/methylmethacrylic acid copolymers, the alkylacrylamide/acrylic acid/alkyl-aminoalkyl(meth)acrylic acid copolymers, the alkylacrylamide/methacrylic acid/alkylamino(meth)acrylic acid copolymers, the alkylacrylamide/methylmethacrylic acid/alkylaminoalkyl(meth)acrylic acid copolymers, the acrylamide/alkylmethacrylate/alkylaminoethylmethacrylate/alkyl methacrylate copolymers and the copolymers of unsaturated carboxylic acids, cationically derivatized unsaturated carboxylic acids and optionally other ionic or nonionic polymers.

Preferred usable zwitterionic polymers are derived from the group of acrylamidoalkyltrialkylammonium chloride/acrylic acid copolymers and their alkali and ammonium salts, the acrylamidoalkyltrialkylammonium chloride/methacrylic acid copolymers and their alkali and ammonium salts, and the methacryloylethylbetaine/methacrylate copolymers.

Further preferred are amphoteric polymers that comprise, along with one or more anionic monomers, methacrylamidotrialkylammonium chloride and dimethyl(diallyl)ammonium chloride as cationic monomers.

Specially preferred amphoteric polymers are derived from the group of methacrylamido-alkyl-trialkylammonium chloride/dimethyl(diallyl)ammonium chloride/acrylic acid copolymers, the methacrylamidoalkyltrialkylammonium chloride/dimethyl(diallyl)ammonium chloride/methacrylic acid copolymers and the methacrylamidoalkyltrialkylammonium chloride/dimethyl(diallyl)ammonium chloride/alkyl(meth)acrylic acid copolymers and their alkali and ammonium salts.

Amphoteric polymers from the group of the methacrylamidopropyltrimethylammonium chloride/dimethyl(diallyl)ammonium chloride/acrylic acid copolymers, the methacrylamidopropyltrimethylammonium chloride/dimethyl (diallyl)ammoniurn chloride/acrylic acid copolymers and the methacrylamidopropyltrimethylammonium chloride/dimethyl(diallyl)ammonium chloride/alkyl(meth)acrylic acid copolymers and their alkali and ammonium salts are especially preferred.

Laundry detergents or cleaners can comprise the previously named cationic and/or amphoteric polymers preferably in proportions between 0.01 and 10% by weight, based in each case on the total weight of the laundry detergent or cleaning agent. However, in the context of the present invention, those detergents or cleaning agents are preferred in which the proportion of cationic and/or amphoteric polymers is between 0.01 and 8% by weight, preferably between 0.01 and 6% by weight, preferably between 0.01 and 4% by weight, especially preferably between 0.01 and 2% by weight, and particularly between 0.01 and 1% by weight, based in each case on the total weight of the machine dishwashing agent. Preferred agents can also be entirely free of cationic and/or amphoteric polymers.

Polymers that act as water softeners are, for example, the polymers that contain sulfonic acid groups. They can be used with special preference.

Copolymers of unsaturated carboxylic acids, monomers containing sulfonic acid groups and optionally other ionic or nonionic monomers are specially preferred as polymers containing sulfonic acid groups.

In the context of the present invention, unsaturated carboxylic acids of the formula $$R^1(R^2)C{=}C(R^3)COOH$$

are preferred, in which $R^1$ to $R^3$ are, independently of each other, a straight-chain or branched saturated alkyl group with 2 to 12 carbon atoms, a straight-chain or branched, singly or multiply unsaturated alkenyl group with 2 to 12 carbon atoms, an —$NH_2$, —OH, or —COOH substituted alkyl or alkenyl group or or $COOR^4$ in which $R^4$ is a saturated or unsaturated, linear or branched hydrocarbon group with 1 to 12 carbon atoms.

Of the unsaturated carboxylic acids that can be described by the preceding formula, acrylic acid ($R^1{=}R^2{=}R^3{=}H$), methacrylic acid ($R^1{=}R^2{=}H$; $R^3{=}CH_3$) and/or maleic acid ($R^1{=}COOH$; $R^2{=}R^3{=}H$) are preferred.

Among the monomers containing sulfonic acid groups, those are preferred that have the formula $$R^5(R^6)C{=}C(R^7){-}X{-}SO_3H$$

in which $R^5$ to $R^7$, independently of each other, stand for —H, —$CH_3$, a straight-chain or branched saturated alkyl group with 2 to 12 carbon atoms, a straight-chain or branched, singly or multiply unsaturated alkenyl group with 2 to 12 carbon atoms, an —$NH_2$, —OH, or —COOH substituted alkyl or alkenyl group or or $COOR^4$ in which $R^4$ is a saturated or unsaturated, linear or branched hydrocarbon group with 1 to 12 carbon atoms and X stands for an optionally present spacer group selected from —$CH_2)_n$— with n=0 to 4, —COO—$(CH_2)_k$— with k=1 to 6, —C(O)—NH—$C(CH_3)_2$ and —C(O)—NH—$CH(CH_2CH_3)$—.

Of these monomers, the preferred ones are those having the formulas $$H_2C{=}CH{-}X{-}SO_3H$$

$$H_2C{=}C(CH_3){-}X{-}SO_3H$$

$$HO_3S{-}X{-}(R^6)C{=}C(R^7){-}X{-}SO_3H$$

in which $R^6$ and $R^7$ independently of each other are selected from —H, —$CH_3$, —$CH_2CH_3$, —$CH_2CH_2$—$CH_3$, or —$CH(CH_3)_2$, and X stands for an optionally present spacer group selected from —$(CH_2)_n$— with n=0 to 4, —COO—$(CH_2)_k$— with k=1 to 6, —C(O)—NH—$C(CH_3)_2$ and —C(O)—NH—$CH(CH_2CH_3)$—.

Particularly preferred monomers comprising sulfonic acid groups include 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy)-propane-sulfonic acid, 2-methyl-2-propene-1-sulfonic acid, styrenesulfonic acid, vinylsulfonic acid, 3-sulfopropyl acrylate, 2-sulfopropyl methacrylate, sulfomethacrylamide, sulfomethyl methacrylamide and water-soluble salts of the acids named.

Other ionic or nonionic monomers that can be considered include in particular ethylenically unsaturated compounds. The proportion of these other ionic or nonionic monomers in the polymers used is preferably less than 20% by weight, based on the polymer. Polymers to be used especially preferably consist solely of monomers of the formula $R^1(R^2)C{=}C(R^3)COOH$ and monomers of the formula $R^5(R^6){=}C(R^7){-}X{-}SO_3H$.

In summary, copolymers of i) unsaturated carboxylic acids having the formula $R^1(R^2)C{=}C(R^3)COOH$, in which the $R^1$ to $R^3$ independently of each other stand for —H, —$CH_3$, a straight or branched saturated alkyl group with 2 to 12 carbon atoms, a straight or branched, singly or multiply unsaturated alkenyl group with 2 to 12 carbon atoms, or an —$NH_2$, —OH, or —COOH substituted alkyl or alkenyl group as described above or or $COOR^4$ in which $R^4$ is a saturated or unsaturated, linear or branched hydrocarbon group with 1 to 12 carbon atoms, ii) monomers comprising sulfonic acid groups, having the formula $$R^5(R^6)C{=}C(R^7){-}X{-}SO_3H$$

in which the $R^5$ to $R^7$ independently of each other stand for —H, —$CH_3$, a straight or branched saturated alkyl group having 2 to 12 carbon atoms, a straight or branched, singly or multiply unsaturated alkenyl group having 2 to 12 carbon atoms, an —$NH_2$, —OH, or —COON substituted alkyl or alkenyl group as defined above or or $COOR^4$ in which $R^4$ is a saturated or unsaturated, linear or branched hydrocarbon group with 1 to 12 carbon atoms and X stands for an optionally present spacer group selected from —$(CH_2)_n$— with n=0 to 4, —COO—$(CH_2)_k$— with k=1 to 6, —C(O)—NH—$C(CH_3)_2$— and —C(O)—NH—$CH(CH_2CH_3)$— iii) and optionally other ionic or nonionic monomers are particularly preferred.

Other specially preferred copolymers comprise i) one or more unsaturated carboxylic acids from the group of acrylic acid, methacrylic acid, and maleic acid, ii) one or more monomers containing sulfonic acid groups, having the formulas $$H_2C{-}CH{-}X{-}SO_3H$$

$$H_2C{=}C(CH_3){-}X{-}SO_3H$$

$$HO_3S{-}X{-}(R^6)C{=}C(R^7){-}X{-}SO_3H$$

in which $R^6$ and $R^7$, independently of each other, are selected from —H, —$CH_3$, —$CH_2CH_3$, —$CH_2CH_2CH_3$, and —$CH(CH_3)_2$, and X stands for an optionally present spacer group selected from $—(CH_2)_n—$ with n=0 to 4, $—COO—(CH_2)_k—$ with k=1 to 6, $—C(O)—NH—C(CH_3)_2—$ and $C(O)—NH—CH(CH_2CH_3)—$ iii) optionally other ionic or nonionic monomers.

The copolymers can comprise the monomers of groups i) and ii), and optionally iii), in varying proportions. All the representatives of group i) can be combined with all the representatives of group ii) and with all the representatives of group iii). Especially preferred polymers have certain structural units that will be described in the following.

For instance, copolymers comprising structural units of the formula $$—[CH_2—CHCOOH]_m—[CH_2—CHC(O)—Y—SO_3H]_p—$$

are preferred, in which m and p each stand for a real integer between 1 and 2000, and Y stands for a spacer group selected from substituted or unsubstituted aliphatic, aromatic or substituted aromatic hydrocarbon groups with 1 to 24 carbon atoms, with the preferred spacer groups being those in which Y stands for $—O—(CH_2)_n—$ with n=0 to 4, for $—O—(C_6H_4)—$, for $—NH—C(CH_3)_2—$, or $—NH—CH(CH_2CH_3)—$.

These polymers are made by copolymerization of acrylic acid with an acrylic acid derivative comprising sulfonic acid groups. If one copolymerizes that sulfonic acid-comprising acrylic acid derivative with methacrylic acid, one gets a different polymer, the use of which is also preferred. The corresponding copolymers comprise structural units having the formula $$—[CH_2—C(CH_3)COOH]_m—[CH_2—CHC(O)—Y—SO_3H]_p—$$

in which m and p each stand for a real integer between 1 and 2000 and Y stands for a spacer group that is selected from substituted or unsubstituted aliphatic, aromatic or substituted aromatic hydrocarbon groups with 1 to 24 carbon atoms, with the preferred spacer groups being those in which Y stands for $—O—(CH_2)_n—$ with n=0 to 4, for $—O—(C_6H_4)—$, for $—NH—C(CH_3)_2—$, or $—NH—CH(CH_2CH_3)—$.

Entirely analogously, acrylic acid and/or methacrylic acid can also be copolymerized with methacrylic acid derivatives that contain sulfonic acid groups, thus changing the structural units in the molecule. Thus one can get specially preferred copolymers having structural units of the formula $$—[CH_2—CHCOOH]_m—[CH_2—C(CH_3)C(O)—Y—SO_3H]_p—$$

in which m and p each stand for a real integer between 1 and 2000 and Y stands for a spacer group that is selected from substituted or unsubstituted aliphatic, aromatic or substituted aromatic hydrocarbon groups with 1 to 24 carbon atoms, with the preferred spacer groups being those in which Y stands for $—O—(CH_2)_n—$ with n=0 to 4, for $—O—(C_6H_4)—$, for $—NH—C(CH_3)_2—$, or $—NH—CH(CH_2CH_3)—$. Copolymers are also preferred that have structural units of the formula $$—[CH_2—C(CH_3)COOH]_m—[CH_2—C(CH_3)C(O)—Y—SO_3H]_p—$$

in which m and p each stand for a real integer between 1 and 2000 and Y stands for a spacer group that is selected from substituted or unsubstituted aliphatic, aromatic or substituted aromatic hydrocarbon groups with 1 to 24 carbon atoms, with the preferred spacer groups being those in which Y stands for $—O—(CH_2)_n—$ with n=0 to 4, for $—O—(C_6H_4)—$, for $—NH—C(CH_3)_2—$, or $—CH(CH_2CH_3)—$.

Instead of, or in addition to, acrylic acid and/or methacrylic acid, maleic acid can also be used as a particularly preferred monomer of group 1). In this way, one arrives at copolymers preferred according to the invention which comprise structural units having the formula $$—[HOOCCH—CHCOOH]_m—[CH_2—CHC(O)—Y—SO_3H]_p—$$

in which m and p each stand for a real integer between 1 and 2000 and Y stands for a spacer group that is selected from substituted or unsubstituted aliphatic, aromatic or substituted aromatic hydrocarbon groups with 1 to 24 carbon atoms, with the preferred spacer groups being those in which Y stands for $—O—(CH_2)_n—$ with n=0 to 4, for $—O—(C_6H_4)—$, for $—NH—C(CH_3)_2—$, or $—NH—CH(CH_2CH_3)—$. Copolymers are also preferred that have structural units of the formula $$—[HOOCCH—CHCOOH]_m—[CH_2—C(CH_3)C(O)O—Y—SO_3H]_p—$$

in which m and p each stand for a real integer between 1 and 2000 and Y stands for a spacer group that is selected from substituted or unsubstituted aliphatic, aromatic or substituted aromatic hydrocarbon groups with 1 to 24 carbon atoms, with the preferred spacer groups being those in which Y stands for $—O—(CH_2)_n—$ with n=0 to 4, for $—O—(C_6H_4)—$, for $—NH—C(CH_3)_2—$, or $—CH(CH_2CH_3)—$.

In summary, the copolymers preferred are those that comprise structural units having the formulas $$—[CH_2—CHCOOH]_m—[CH_2—CHC(O)—Y—SO_3H]_p—$$

$$—[CH_2—C(CH_3)COOH]_m—[CH_2—CHC(O)—Y—SO_3H]_p—$$

$$—[CH_2—CHCOOH]_m—[CH_2—C(CH_3)C(O)—Y—SO_3H]_p—$$

$$—[CH_2—C(CH_3)COOH]_m—[CH_2—C(CH_3)C(O)—Y—SO_3H]_p—$$

$$—[HOOCCH—CHCOOH]_m—[CH_2—CHC(O)—Y—SO_3H]_p—$$

$$—[HOOCCH—CHCOOH]_m—[CH_2—C(CH_3)C(O)O—Y—SO_3H]_p—$$

in which m and p each stand for a real integer between 1 and 2000 and Y stands for a spacer group that is selected from substituted or unsubstituted aliphatic, aromatic or substituted aromatic hydrocarbon groups with 1 to 24 carbon atoms, with the preferred spacer groups being those in which Y stands for $—O—(CH_2)_n—$ with n=0 to 4, for $—O—(C_6H_4)—$, for $—NH—C(CH_3)_2—$, or $—NH—CH(CH_2CH_3)—$.

The sulfonic acid groups in the polymers can be partially or entirely in the neutralized form. That is, the acidic hydrogen atom of the sulfonic acid group can, in some or all the sulfonic acid groups, be replaced by metal ions, preferably metal ions and particularly sodium ions. Use of partially of entirely neutralized copolymers comprising sulfonic acid groups is preferred according to the invention.

The monomer distribution of the copolymers preferably used according to the invention is preferably 5 to 95% by weight each of i) or ii) for copolymers that comprise only monomers of groups i) and ii); especially preferably 50 to 90% by weight monomer from group I) and 10 to 50% by weight of monomer from group ii), based on the polymer in each case.

Of the terpolymers, those comprising 20 to 85% by weight monomer from group i), 10 to 60% by weight monomer from group ii) and 5 to30% by weight from group iii) are especially preferred.

The molecular weights of the sulfo-copolymers preferably used according to the invention can be varied to adapt the properties of the polymer to the desired application. Preferred laundry detergents or cleaners are characterized by the copolymers having molecular weights of 2,000 to 200,000 g/mole, preferably 4,000 to 25,000 g/mole, and particularly 5,000 to 15,000 g/mole.

Bleaching agents are substances with washing or cleaning action that can be used with special preference. Of the compounds that produce $H_2O_2$ in water and act as bleaching agents. sodium percarbonate, sodium perborate tetrahydrate and sodium perborate monohydrate are particularly important. Examples of other usable bleaching agents include peroxypyrophosphate, citrate perhydrate, and peracid salts or peracids such as perbenzoate, peroxophthalate, diperazelaic acid, phthaliminoperacid or diperdodecanedioic acid that provide $H_2O_2$. It is also possible to use bleaching agents of the group of organic bleaching agents. Typical organic bleaching agents are the diacyl peroxides such as dibenzoyl peroxide. Other typical organic bleaching agents are the peroxy acids, of which the alkyl peroxyacids and aryl peroxyacids must be mentioned in particular as examples. Preferred representatives that can be used are (a) peroxybenzoic acid and its ring-substituted derivatives such as alkylperoxybenzoic acids, as well as peroxy-α-naphthoic acid and magnesium mono-perphthalate; (b) the aliphatic or substituted aliphatic peroxyacids, such as peroxylauric acid, peroxystearic acid, ϵ-phthalimidoperoxycapric acid, [phthaliminoperoxyhexanoic acid, (PAP)], o-carboxybenzamidoperoxycapric acid, N-nonenylamidoperadipic acid and N-nonenylamidopersuccinate, and (c) aliphatic and araliphatic peroxydicarboxcylic acids such as 1,12-diperoxycarboxylic acid, 1,9-diperoxyazelaic acid, diperoxysebacic acid, diperoxybrassylic acid, the diperoxyphthalic acids, 2-decyldiperoxybutan-1,4-dioic acid, and N,N-terephthaloyl-di(6-aminopercapric acid).

Substances that release chlorine or bromine can also be used as bleaching agents. The suitable materials that release chlorine or bromine that can be considered include, for instance, heterocyclic N-bromamides and N-chloramides, such as trichloroisocyanuric acid, tribromoisocyanuric acid, dibromoisocyanuric acid and/or dichloroisocyanuric acid (DICA) and/or their salts with cations such as potassium and sodium. Hydantoin compounds, such as 1,3-dichloro-5,5-dimethylhydantoin are also suitable.

Laundry detergents or cleaners that contain 1 to 35% by weight, preferably 2.5 to 30% by weight, especially preferably 3.5 to 30% by weight and particularly 5 to 15% by weight bleaching agent, preferably sodium percarbonate, are preferred according to the invention.

The active oxygen content of the laundry detergent or cleaner is preferably between 0.4 and 10% by weight, especially preferably between 0.5 and 8% by weight, and particularly between 0.6 and 5% by weight, based in each case on the total weight of the laundry detergent or cleaner. Specially preferred agents have an active oxygen content greater than 0.3% by weight, preferably above 0.7% by weight, especially preferably above 0.8% by weight and particularly above 1.0% by weight.

Bleach activators are used in laundry detergents or cleaners, for example, to get good bleaching action in washing at temperatures of 60° C. and below. Compounds that yield aliphatic peroxocarboxylic acids with preferably 1 to 10 C atoms, especially 2 to 4 C atoms and/or optionally substituted perbenzoic acid, under perhydrolysis conditions can be used as bleach activators. Substances bearing O-acyl and/or N-acyl groups of the specified number of C atoms and/or optionally substituted benzoyl groups are suitable. Multiply acylated alkylenediamines are preferred, especially tetraacetylethylenediamine (TAED), acylated triazine derivatives, especially 1,5-diacetyl-1,4-dioohexahydro-1,3,5-triazine (DADHT), acylated glycolurils, especially tetraacetylglycoluril (TAGU), N-acylimides, especially N-nonanoylsuccinimide (NOSI), acylated phenolsulfonates, especially n-nonanoyl- or iso-nonanoyl-oxybenzenesulfonate (n- or iso-NOBS), carboxylic acid anhydrides, especially phthalic anhydride, acylated multifunctional alcohols, especially triacetin, ethylene glycol diacetate, isopropenyl acetate, 2,5-diacetoxy-2,5-dihydrofuran.

Other bleach activators used preferably in the context of the present invention are compounds from the group of cationic nitriles, especially cationic nitriles having the formula

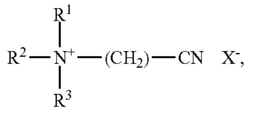

in which $R^1$ stands for —H, —$CH_3$, a $C_{2-24}$-alkyl or alkenyl group, a substituted $C_{2-24}$-alkyl or alkenyl group having at least one substituent from the group —Cl, —Br, OH, —$NH_2$, —CN, an alkyl or alkenylaryl group with a $C_{1-24}$-alkyl group and at least one other substituent on the aromatic ring, or for a substituted alkyl or alkenylaryl group having at least one other substituent on the aromatic ring, $R^2$ and $R^3$, independently of each other, are selected from —$CH_2$—CN, —$CH_3$, —$CH_2CH_3$, —$CH_2CH_2CH_3$, —$CH(CH_3)$—$CH_3$, —$CH_2OH$, —$CH_2$—$CH_2$—OH, —$CH(OH)CH_3$, —$CH_2$—$CH_2$—$CH_2$—OH, —$CH_2$—$CH(OH)$—$CH_3$, —$CH(OH)$—$CH_2CH_3$, —$CH_2CH_2$—$O)_nH$ with n=1, 2, 3, 4, 5 or 6, and X is an anion.

A cationic nitrile having the formula

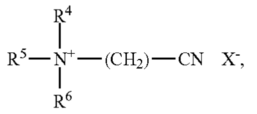

is specially preferred in which $R^4$, $R^5$ and $R^6$ independently of each other are selected from —$CH_3$, —$CH_2CH_3$, —$CH_2CH_2CH_3$, or —$CH(CH_3)$_$CH_3$, in which $R^4$ can also be —H and X is an anion, and preferably $R^5$=$R^6$=—$CH_3$, and especially $R^4$=$R^5$=$R^6$=—$CH_3$, and compounds of the formulas $(CH_3)_3N^{(+)}CH_2$—$CNX^-$, $(CH_3CH_2)_3N^{(+)}CH_2$—$CNX^-$, $(CH_3CH_2CH_2)_3{}^{(+)}CH_2$—$CNX^-$, $(CH_3CH(CH_3))_3N^{(+)}CH_2$—$CNX^-$, or $(HO$—$CH_2$—$CH_2)_3N^{(+)}CH_2$—$CNX^-$ are especially preferred, in which again, of the group of these substances, the cationic nitrile of the formula $(CH_3)_3N^{(+)}CH_2$—$CNX^-$, in which $X^-$ stands for an anion selected from the group of chloride, bromide, iodide, bisulfate, methosulfate, toluenesulfonate(tosylate) or xylenesulfonate is especially preferred.

Compounds which under perhydrolysis conditions yield aliphatic peroxocarboxylic acids with preferably 1 to 10 carbon atoms, especially 2 to 4 carbon atoms, and/or atoms, especially 2 to 4 carbon atoms, and/or optionally substituted perbenzoic acids, can also be used as bleach activators. Substances that bear O-acyl and/or N-acyl groups of the stated number of carbon atoms and/or optionally substituted benzoyl groups are suitable. The preferred compounds are multiply acylated alkylenediamines, especially tetraacetylethylenediamine (TAED), acylated triazine derivatives, especially 1,5-diacetyl-2,4-dioxohexahydro-1,3,5-triazine (DADHT), acylated glycourils, especially tetraacetylglycouril (TAGU), N-acyl imides, especially N-nonanoylsuccinimide (NOSI), acylated phenolsulfonates, especially n-nonanoyloxybenzenesulfonate or iso-nonanoyloxybenzenesulfonate (n- or iso-NOBS), carboxylic acid anhydrides, especially phthalic anhydride, acylated multifunctional alcohols, especially triacetin, ethylene glycol diacetate, 2,5-diacetoxy-2,5-dihydrofuran, N-methylmorpholinium-acetonitrile-methylsulfate (MMA) as well as acetylated sorbitol and mannitol or mixtures of them (SORMAN), acylated sugar derivatives, especially pentaacetyl glucose (PAG), pentaacetyl fructose, tetraacetyl xylose and octaacetyl lactose, as well as acetylated, optionally N-alkylated glucamines and gluconolactones, and/or N-acylated lactams, such as N-benzoyl caprolactam. Hydrophilically substituted acylacetals and acyllactams are likewise used preferably. Combinations of conventional bleach activators can also be used.

To the extent that bleach activators other than the optional nitrilquats are to be used, it is preferable to use bleach activators from the group of multiply acylated alkylenediamines, especially tetraacetylethylenediamine (TAED), N-acyl imides, especially N-nonanoylsuccinimide (NOSI), acylated phenolsulfonates, especially n-nonanoyloxybenzenesulfonate or iso-nonanoyloxybenzenesulfonate (n- or iso-NOBS), N-methylmorpholinium-acetonitrile-methylsulfate (MMA), preferably in proportions of up to 10% by weight, especially 0.1% by weight up to 8% by weight, particularly 2 to 8% by weight and especially preferably 2 to 6% by weight, based in each case on the total weight of the laundry detergent or cleaner containing the bleach activator.

So-called 'bleach catalysts' can also be used Instead of, or in addition to, the conventional bleach activators. These substances are transition metal salts or transition metal complexes such as Mn, Fe, Co, Ru or Mo salene complexes or carbonyl complexes that intensify bleaching. Complexes of Mn, Fe, Co, Ru, Mo, Ti, V and Cu with N-containing tripod ligands, and Co, Fe, Cu and Ru ammine complexes are also usable as bleach activators.

Bleach-intensifying transition metal complexes, especially those having Mn, Fe, Co, Cu, Mo, V, Ti and/or Ru as the central atom, preferably selected from the group of manganese and/or cobalt salts and/or complexes, especially preferably the cobalt(ammine) complexes, the cobalt(acetato) complexes, the cobalt(carbonyl) complexes, and the chlorides of cobalt or of manganese, of manganese sulfate, can optionally be used in the usual proportions, preferably in a proportion up to 5% by weight, especially from 0.0025% by weight to 1% by weight and especially preferably from 0.01% by weight to 0.25% by weight, based in each case on the total weight of the laundry detergent or cleaner containing the bleach activator. In special cases, though, even more bleach activator can be used.

Enzymes can be used to increase the washing or cleaning ability of laundry detergents or cleaners. Those include in particular proteases, amylases, lipases, hemicellulases, cellulases or oxidoreductases, and, preferably, mixtures of them. These enzymes are of natural origin in principle. Improved variants, based on the natural molecules, are available for use in laundry detergents and cleaners. They are preferably used appropriately. Laundry detergents or cleaners contain enzymes preferably in total proportions of $1\cdot10^{-6}$ to 5% by weight, based on the active protein. The protein concentration can be determined with known methods, such as the BCA procedure or the biuret procedure.

Of the proteases, those of the subtilisin type are preferred. Examples of those include the subtilisins BPN' and Carlsberg, Protease PB92, subtilisins 147 and 309, the alkaline protease from *Bacillus lentus*, subtilisin DY and the subtilases, but not the enzymes thermitase, Proteinase K, and the proteases TW3 and TW7, which are no longer classified with the subtilisins in the narrower sense. Subtilisin Carlsberg, in the further-developed form, is available from Novozymes A/S, Bagsvrd, Denmark, under the trade name Alcalase®. Subtilisins 147 and 309 are offered as Esperase® or Savinase® by Novozymes. The variants listed under the designation BLAP® by Novozymes. The variants listed under the designation BLAP® are derived from the protease of *Bacillus lentus* DSM 5483.

Examples of other usable proteases are those available under the trade names Durazym®, Relase®, Everlase®, Nafizym, Natalase®, Kannase® and Ovozymes® from Novozymes; those available under the trade names Purafect®, Purafect®, OxP and Properase from Genencor; those available under the trade name of Protosol® from Advanced Biochemical Ltd., Thane, India; those available under the trade name Wuxi® from Wuxi Snyder Bioproducts Ltd., China; those available under the trade names Proleather® and Protease P® from Amano Pharmaceuticals, Ltd., Nagoya, Japan; and those available under the trade name Proteinase K-16 from Kao Corp., Tokyo, Japan.

Examples of amylases usable according to the invention include the α-amylases of *Bacillus licheniformis, B. amyloliquefaciens* or *B. stearothermohilus*, as well as the improvements on them for use in laundry detergents and cleaners. The enzyme from *B. licheniformis* is available from Novozymes as Termamyl®, and from Genencor as Purastar® ST. Further developments of these α-amylases are available from Novozymes as Duramyl® and Termamyl® ultra; from Genencor as Purastar® OxAm, and from Daiwa Seiko Inc., Tokyo, Japan, as Keistase®. The α-amylase from *B. amyloliquefaciens* is offered by Novozymes as BAN®, and variants derived from the α-amylase from *B. stearothermophilus* are offered as BSG® and Novamyl®, likewise from Novozymes.

The α-amylase from *Bacillus* sp. A 7-7 (DSM 12368) and the cyclodextrin-glucanotransferase (CGTase) from *B. agaradherens* (DSM 9948) are also recommended for this purpose.

The improvements of the α-amylase from *Aspergillus niger* and *A. oryzae* obtainable from Novozymes as Fungamyl® are also suitable. Amylase-LT® is another commercial product.

Lipases or cutinases are also usable according to the invention, especially because of their triglyceride-hydrolyzing activities, but also to generate peracids in situ from suitable precursors. These include, for example, the lipases originally available from *Humicola lanuginosa* (*Thermomyces lanuginosus*), or further-developed lipases, especially those with the amino acid replacement D96L. They are marketed by Novozymes, for example, under the trade names Lipolase®, Lipolase® Ultra, LipoPrime®, Lipozyme® and Lipex®. Cutinases originally isolated from *Fusarium solani pisi* and *Humicola insolens* are also usable, for example. Similarly usable lipases are available from Amano under the names Lipase CE. Similarly usable lipases are available from Amano under the names Lipase CE®, Lipase P®, Lipase B®, or Lipase CES®, Lipase AKG®, *Bacillus* sp. Lipase®, Lipase AP®, Lipase M-AP® and Lipase AML®. The lipases or cutinases from Genencor are also usable, for example.

Their starting enzymes were originally isolated from *Pseudomonas mendocina* and *Fusarium solanii*. Other important commercial products that must be mentioned are the preparations M1 Lipase® and Lipomax® originally marketed by Gist-Brocades and the enzymes marketed by Meito Sangyko KK, Japan, as Lipase MY-30®, Lipase OF® and Lipase PL®, as well as the Genencor product Lumafast®.

Enzymes classified as hemicellulases can also be used. They include, for example, mannanases, xanthanlyases, pectinlyases (=pectinases), pectin esterases, pectate lyases, xyloglucanases (=Xylanases), pullulanases and β-glucanases. Suitable mannanases are available, for example, as Gamanase® and Pectinex AR® from Novozymes, as Rohapec® B1L from AB Enzymes and as Pyrolase® from Diversa Corp., San Diego, Calif., USA. The β-glucanase obtained from *B. subtilis* is available as Cereflo® from Novozymes.

Oxidoreductases, such as oxidases, oxygenases, catalases, peroxidases such as halo-, chloro-, bromo-, ligno-, glucose- or manganese peroxidases, dioxygenases or laccases (phenol oxidases, polyphenol oxidases) can be used according to the invention to increase the bleaching action. Denilite® 1 and 2 from Novozymes must be mentioned as suitable commercial products. It is advantageous to add additional preferably organic, especially preferably aromatic compounds that interact with the enzymes to strengthen the activity of the oxidoreductases in question (enhancers) or to assure electron flow when the redox potentials of the oxidizing enzymes and the dirt are greatly different (mediators).

The enzymes are, for example, either produced originally from microorganisms, such as those of the genera *Bacillus, Streptomyces, Humicola* or *Pseudomonas*, and/or are produced by suitable microorganisms by biotechnological processes that are themselves known, such as by transgenic expression hosts of the genera *Bacillus* or filamentous fungi.

The enzymes under consideration are preferably purified by processes that are themselves established, for example, by precipitation, sedimentation, concentration, filtration of the liquid phases, microfiltration, ultrafiltration, action of chemicals, deodorization or suitable combinations of those steps.

The enzymes can be used in any of the forms established at the state of the art. That includes, for instance, the solid preparations obtained by granulation, extrusion or lyophilization or, particularly for agents in liquid or gel forms, solutions of the enzyme, advantageously as concentrated as possible, low in water and/or mixed with stabilizers.

Alternatively, the enzymes can be encapsulated for both the liquid and solid use forms, such as by spray drying or extrusion of the enzyme solution together with a preferably natural polymer or in the form of capsules, such as those in which the enzyme is enclosed as in a solidified gel or in those of the core-shell, type in which the enzyme-containing core is coated with a protective layer that is impermeable to water, air and/or chemicals. Other additional active ingredients such as stabilizers, emulsifiers, pigments, bleaches or colorants can be applied in layered shells. Such capsules are applied by methods that are themselves known, such as by shaking or rolling granulation or in fluidized bed processes. Such granulations are advantageously low in dust and stable in storage because of the coating, for example, by application of polymeric film-formers.

It is further possible to formulate two or more enzymes together so that a single granulation has multiple enzyme activities.

A protein or an enzyme can be protected, particularly during storage, against damages such as inactivation, denaturation or decomposition due to physical influences, oxidation, or proteolytic hydrolysis. If the proteins and/or enzymes are obtained microbiologically, inhibition of proteolysis is especially preferred, particularly if the agent also contains proteases. Laundry detergents or cleaners can contain stabilizers for that purpose. Provision of such an agent is a preferred embodiment of the present invention.

Reversible protease inhibitors are one group of stabilizers. Benzamidine hydrochloride, borax, boric acids, boronic acids, or their salts or esters are often used, including in particular derivatives having aromatic groups, such as ortho-substituted, meta-substituted and para-substituted phenylboronic acids or their salts or esters. Ovomucoid and leupeptin, among others, must be mentioned as peptidic protease inhibitors. Formation of fusion proteins from proteases and peptide inhibitors is another option.

Other enzyme stabilizers include aminoalcohols such as mono-, di- and tri-ethanolamine and -propanolamine and mixtures of them, aliphatic carboxylic acids up to $C_{12}$, such as succinic acid, other dicarboxylic acids or salts of the acids named. End-group-capped fatty acid amide alkoxylates are also suitable. Certain organic acids used as builders can also stabilize a contained enzyme.

Lower aliphatic alcohols, but especially polyols such as glycerol, ethylene glycol, propylene glycol or sorbitol are other enzyme stabilizers that are often used. Calcium salts such as calcium acetate or calcium formate, and magnesium salts, are also used.

Polyamide oligomers or polymeric compounds such as lignin, water-soluble vinyl copolymers or cellulose ethers, acrylic polymers and/or polyamides stabilize enzyme preparations against physical influences or pH fluctuations, among other things. Polymers containing polyamine-N-oxides act as enzyme stabilizers. The linear $C_8$-$C_{18}$ polyoxyalkylenes are other polymeric stabilizers. Alkyl polyglycosides can stabilize the enzymic components and can even increase their activity. Cross-linked nitrogenous compounds likewise act as enzyme stabilizers.

Reducing agents and antioxidants increase the stability of the enzymes against oxidative decomposition. Sodium sulfite is a sulfur-containing reducing agent, for example.

It is preferred to use combinations of stabilizers, for example, combinations of polyols, boric acid and/or borax, the combination of boric acid or borate, reducing salts and succinic acid or other dicarboxylic acids, or the combination of boric acid or borate with polyols or polyamino compounds and with reducing salts. The action of peptide-aldehyde stabilizers is increased by the combination with boric acid and/or boric acid derivatives and polyols, and is further increased by the additional use of divalent cations such as calcium ions.

It is preferred to use one or more enzymes or enzyme preparations, preferably solid protease preparations and/or amylase preparations, in proportions of 0.1 to 5% by weight, preferably of 0.2 to 4.5% by weight, and particularly 0.4 to 4% by weight, based in each case on the total enzyme-containing agent.

It is possible to incorporation disintegrants, so-called 'tablet explosives', in these agents to make the breakup of solids easier, so as to shorten the disintegration times. According to Römpp ($9^{th}$ Ed., Vol. 6, p. 4440) and Voigt, "*Lehrbuch der pharmazeutischen Technologie" ["Textbook of pharmaceutical technology*"] ($6^{th}$ Ed., 1987, pages 182-184), 'tablet explosives' or disintegration accelerators are understood to be additives that provide for rapid disintegration of tablets in water or in gastric fluid and for release of pharmaceuticals in absorbable form.

These substances, which are called "explosive" agents because of their action, increase in volume on entry of water. On one hand, they increase their own volume (swelling). On the other hand, release of gases can produce a pressure that breaks the tablets into smaller particles. Carbonate/citric acid systems are disintegrants that have been known for a long time, and other organic acids can also be used. Examples of swelling disintegrants include synthetic polymers such as polyvinylpyrrolidone (PVP) or natural polymers or modified natural substances such as celluloses and starches and their derivatives, alginates, or casein derivatives.

Disintegrants can be used preferably in proportions of 0.5 to 10% by weight, preferably 3 to 7% by weight, and particularly 4 to 6% by weight, based in each case on the total weight of the agent containing the disintegrant.

Disintegrants based on cellulose are used as preferred disintegrants, so that preferred laundry detergents or cleaners contain such a cellulose-based disintegrant in proportions of 0.5 to 10% by weight, preferably 3 to 7% by weight, and particularly 4 to 6% by weight. Pure cellulose has the empirical composition $(C_6H_{10}O_5)_n$. Considered formally, it is a β-1,4-polyacetal of cellobiose which is itself made up of two molecules of glucose. Suitable celluloses comprise about 500 to 5000 glucose units, and accordingly have average molecular weights of 50,000 to 500,000. Cellulose-based disintegrants usable in the context of the present invention also include cellulose derivatives that can be obtained from cellulose by polymer-like reactions. Such chemically modified celluloses include, for example, products of esterifications or etherifications, in which hydroxyl hydrogen atoms are substituted. However, celluloses in which the hydroxy groups are replaced by functional groups not bound through an oxygen atom can also be used as cellulose derivatives. The group of cellulose derivatives includes, for example, alkali celluloses, carboxymethylcellulose (CMC), cellulose esters and ethers, and amino celluloses. The cellulose derivatives named are preferably not used alone as cellulose-based disintegrants, but in mixtures with cellulose. The proportion of cellulose derivatives in these mixtures is preferably less than 50% by weight, especially preferably less than 20% by weight, based on the cellulose-based disintegrant. It is particularly preferable to use, as cellulose-based disintegrants, pure cellulose that is free of cellulose derivatives.

The cellulose used as a disintegrant additive is preferably not used in finely divided form, but converted into a coarser form before mixing into the premixes to be pressed, such as granulated or compacted. The particle sizes of such disintegrants are usually greater than 200 μm, preferably with at least 90% by weight between 300 and 1600 μm and particularly with at least 90% by weight between 400 and 1200 μm. The coarser cellulose-based disintegrants named above and described in more detail in the documents cited are used preferably in the context of the present invention. They are commercially available, for example, as Arbocel® TF-30-HG from the Rettenmaier company.

Microcrystalline cellulose can be used as a further cellulose-based disintegrant or as an ingredient of those components. This microcrystalline cellulose is obtained by partial hydrolysis of cellulose under conditions such that only the amorphous regions of the cellulose (ca. 30% of the total cellulose) are attacked and completely dissolved while the crystalline regions (ca. 70%) remain undamaged. Subsequent disaggregation of the microfine cellulose resulting from the hydrolysis gives the microcrystalline celluloses, which have primary particle sizes of about 5 μm and which can, for instance, be compacted into granulations having an average particle size of 200 μm.

Preferred disintegrants, preferably a disintegrant based on cellulose, preferably in a granular, cogranular or compacted form, can be contained in agents that contain disintegrants in proportions of 0.5 to 10% by weight, preferably 3 to7% by weight, and particularly 4 to 6% by weight, based in each case on the total weight of the agent containing the disintegrant.

Effervescent systems that evolve gases can also be preferred tablet disintegrants according to the invention. The effervescent gas-evolving systems can consist of a single substance that releases gas on contact with water. Of these compounds, magnesium peroxide in particular must be named. It releases oxygen on contact with water. Usually, though, the gas-evolving effervescent system itself comprises at least two components which react with each other, forming gas. Although many systems are conceivable and feasible, releasing, for example nitrogen, oxygen or hydrogen, the effervescent gas-evolving system used in detergents or cleaning agents is chosen from both economic and ecological viewpoints. Preferred effervescent systems comprise alkali metal carbonate and/or bicarbonate, and an acidifying agent that is suitable to release carbon dioxide from the alkali metal salts in aqueous solution.

Of the alkali metal carbonates or bicarbonates, the sodium and potassium salts are definitely preferred over the other salts for reasons of cost. Obviously, it is not necessary to use the pure alkali metal carbonates or bicarbonates; rather, mixtures of different carbonates and bicarbonates can be preferred.

As an optional effervescent system, it is preferable to use 2 to 20% by weight, preferably 3 to 15% by weight, and particularly 5 to 10% by weight of an alkali metal carbonate or bicarbonate, and 1 to 15, preferably 2 to 12% by weight, and particularly 3 to 10% by weight of an acidifying agent, based in each case on the total weight of the agent.

For example, boric acid and alkali metal bisulfates, alkali metal dihydrogen phosphates and other inorganic salts can be used as acidifying agents that release carbon dioxide from the alkali salts in aqueous solution. To be sure, it is preferable to use organic acidifying agents, with citric acid a specially preferred acidifying agent. However, other solid mono-, oligo- and poly-carboxylic acids in particular can also be used. Of this group, again, tartaric acid, succinic acid, malonic acid, adipic acid, maleic acid, fumaric acid, oxalic acid and polyacrylic acid are preferred. Organic sulfonic acids such as amidosulfonic acid are also usable. Sokalan® DCS (BASF trademark), a mixture of succinic acid (up to 31% by weight), glutaric acid (up to 50% by weight) and adipic acid (up to 33% by weight) is commercially available and also preferably usable as an acidifying agent in the context of the present invention.

The preferred acidifying agents in the effervescent system are from the group of organic di- tri- and oligo-carboxylic acids or mixtures of them.

Preferred colorants, the selection of which presents no problem to those skilled in the art, have high storage stability and low sensitivity to the other ingredients of the agent or to light. They do not have any distinct substantivity for the substrates to be treated with the colorant-containing agent, such as textiles, glass, or ceramic or plastic tableware, so as not to stain them.

In selection of the colorant, one must take into consideration the fact that the colorants, in the case of laundry detergents, must not have excessive affinity to textile surfaces, particularly to plastic fibers, while in the case of cleaners one must avoid excessive affinity to glass, ceramic or plastic tableware. At the same time, in selection of suitable colorants, one must consider that colorants have different degrees of stability to oxidation. In general, water-insoluble colorants are more stable to oxidation than are water-soluble colorants. The concentration of the colorants in laundry detergents or cleaners varies, depending on their solubility and on their sensitivity to oxidation. For colorants with good water solubility, such as the Basacid® Green mentioned above, or Sandolan® Blue, also mentioned above, one typically chooses colorant concentrations in the range of a few hundredths to thousandths of one percent by weight. For the pigment colorants, which are specially preferred because of their brilliance, but are less water-soluble, such as the Pigmosol® colorants mentioned above, the suitable concentration of the colorant in laundry detergents or cleaners is, on the other hand, typically a few thousandths to ten-thousandths of one percent by weight.

Preferred colorants are those that can be oxidatively destroyed in the washing process, and mixtures of those with suitable blue colorants, the so-called bluing agents. It has proven advantageous to use colorants that are soluble in water or, at room temperature, in liquid organic substances. For instance, anionic colorants, such as anionic nitroso dyes are suitable. For instance, one possible colorant is Naphthol Green (Color Index (CI) Part 1: Acid Green 1; Part 2: 10020) which is available commercially for example, as Basacid® Green 970 from BASF, Ludwigshafen, or mixtures of it with suitable blue colorants. Other colorants used include Pigmosol® Blue 6900 (CI 74160), Pigmosol® Green 8730 (CI 74260), Basonyl® Red 545 FL (CI 45170), Sandolan® Rhodamin EB400 (CI 45100), Basacid® Yellow 094 (CI 47005), Sicovit® Patent Blue 85E 131 (CI 42051), Acid Blue 183 (CAS 12217-22-0, Cl Acidblue 183), Pigment Blue 15 (CI 74160), Supranol® Blue GLW (CAS 12219-32-8), Nylosan® Yellow N-7GL SGR (CAS 61814-57-1, CI Acidyellow 218) and/or Sandolan® Blue (CI Acid Blue 12219-26-0).

In addition to the preferably usable components described so far, the laundry detergents or cleaners can also contain other ingredients that further improve the application-technology and/or aesthetic properties of these agents. Preferred agents contain one or more substances from the groups of electrolytes, pH-adjusting substances, fluorescent substances, hydrotropes, foam inhibitors, silicone oils, antiredeposition agents, optical brighteners, graying inhibitors, agents to prevent shrinkage, antiwrinkle agents, color transfer inhibitors, antimicrobially active substances, germicides, fungicides, antioxidants, antistatic agents, ironing aids, phobing and impregnating agents, antiswselling and antislip agents, and UV absorbers.

A large number of quite varied salts from the group of inorganic salts can be used as electrolytes. The alkali and alkaline earth metals are preferred cations, while the halides and sulfates are preferred anions. From the viewpoint of production technology, it is preferable to use NaCl or $MgCl_2$ in the laundry detergents or cleaners.

Use of pH-adjusting agents may be indicated to bring the pH of laundry detergents or cleaners to the desired range. All the well-known acids or bases can be used here as long as their use it not ruled out for applications technology or ecologic reasons, or for user protection. The proportion of this adjusting agent usually does not exceed 1% by weight of the total formulation.

Soaps, oils, fats, paraffins or silicone oils can be considered as foam inhibitors. They can optionally be applied to carrier materials. For example, inorganic salts such as carbonates or sulfates, cellulose derivatives, silicates, or mixtures of those materials are suitable carriers. In the context of the present invention, preferred laundry detergents or cleaners contain paraffins, preferably unbranched paraffins (n-paraffins) and/or silicones, preferably linear polymeric silicones, structured as $(R_2SiO)_x$, and called silicone oils. These silicone oils are usually clear, colorless, neutral, odorless, hydrophobic liquids with molecular weights between 1,000 and 150,000, and viscosities between 10 and 1,000,000 mPa·s.

Suitable antiredeposition agents, also called soil repellants, are, for example, nonionic cellulose ethers such as methylcellulose and methylhydroxypropyl-cellulose, with 15 to 30% by weight methoxyl groups and 1 to 15% by weight hydroxypropyl groups, based in each case on the nonionic cellulose ether, and the polymers of phthalic acid and/or terephthalic acid known at the state of the art, or their derivatives, especially polymers of ethylene terephthalate and/or polyethylene glycol terephthalate, or anionically and/or nonionically modified derivatives of them. Of these, the sulfonated derivatives of phthalic acid and terephthalic acid polymers are particularly preferred.

Optical brighteners (so-called "white toners") can be added to laundry detergents or cleaners to prevent graying and yellowing of the textiles treated. These substances adhere to the fibers and cause lightening and simulated bleaching by converting invisible ultraviolet radiation into longer-wave visible light, so that the ultraviolet light absorbed from sunlight is radiated off as a weak bluish fluorescence, which combines with the yellow tone of the grayed or yellowed laundry to give a pure white. Suitable compounds are derived, for example, from the substance classes of the 4,4'-diamino-2,2'-stilbenedisulfonic acids (flavonic acids), 4,4'-distyrylbiphenylenes, methylumbelliferone, coumarins, dihydroquinolines, 1,3-diarylpyrazolines, naphthalic acid imides, benzoxazole, benzisoxazol and benzimidazole systems, and pyrene derivatives with heterocyclic substituents.

Antiredeposition agents have the function of keeping dirt removed from the fibers separated in the liquor, thus preventing readsorption of the dirt. Water-soluble colloids, most of them organic, are suitable for that. Examples include the water-soluble salts of polymeric carboxylic acids, glue, gelatins, salts of ethersulfonic acids of starch or cellulose, or salts of acidic sulfuric acid esters of cellulose or starch. Polyamides having water-soluble acidic groups are also suitable for this purpose. Soluble starch preparations, and starch products other than those named above, such as degraded starch, aldehyde starches, etc., can also be used. Polyvinylpyrrolidone is also usable. Cellulose ethers such as carboxymethylcellulose (sodium salt), methylcellulose, hydroxyalkyl cellulose and mixed ethers such as methyl hydroxyethyl cellulose, methyl hydroxypropyl cellulose, methyl carboxymethyl cellulose, and mixtures of them can also be used as antiredeposition agents.

Synthetic anti-wrinkle agents can be used because textile surface structures, especially those of rayon, rayon staple fiber, cotton, and mixtures of them can tend to wrinkle because the individual fibers are sensitive to bending, kinking, pressing and crushing transverse to the fiber direction. They include, for example, synthetic products based on fatty acids, fatty acid esters, fatty acid amides, fatty acid alkylol ester, fatty acid alkylolamides or fatty alcohols, usually reacted with ethylene oxide, or products based on lecithin or modified phosphoric acid esters.

Phobing and impregnating processes serve to provide the textiles with substances that prevent deposition of dirt or make it easier to wash out. Preferred phobing and impregnating agents include perfluorinated fatty acids, also in the form of their aluminum and zirconium salts, organic silicates, silicones, polyacrylic acid esters with perfluorinated alcohol components or with polymerizable compounds coupled to perfluorinated acyl or sulfonyl groups. Antistatic agents can also be contained. The dirt-repelling finish with phobing and impregnating agents is often classified as an easy-care finish.

Penetration of the impregnating agent in the form of solutions or emulsions of the active substances concerned can be made easier by addition of wetting agents, which reduce the surface tension. Water-repellent finishing of textile goods, tents, surfaces, leather, etc. is another area of application of phobing and impregnating agents. In this case, in contrast to making something water-tight, the pores of the cloth are not closed, so that the material remains able to breathe (hydrophobizing). The hydrophobizing agents used for hydrophobizing coat textiles, leather, paper, wood, etc., with a very thin layer of hydrophobic groups, such as long alkyl chains or siloxane groups. Suitable hydrophobizing agents include, for example, paraffins, waxes, metal soaps, etc. with additions of aluminum or zirconium salts, quaternary ammonium compounds with long-chain alkyl groups, urea derivatives, fatty-acid-modified melamine resins, complex chromium salts, silicones, organotin compounds and glutardialdehyde as well as perfluorinated compounds. The hydrophobized materials do not feel greasy. Nevertheless, water droplets bead up on them, as they do on greased materials, without wetting them. Thus, silicone-impregnated textiles, for example, have a soft hand and repel water and dirt. Spots of ink, wine, fruit juices and the like are more easily removed.

Antimicrobially active substances can be used against microorganisms. Here one distinguishes between bacteriostats, bactericides, fungistats, and fungicides on the basis of their antimicrobial spectrum and their mechanism of action. Examples of important substances of these groups include benzalkonium chloride, alkylarylsulfonates, halophenols and phenylmercuric acetate. Use of these compounds can also be avoided entirely.

The laundry detergents or cleaners can contain antioxidants to prevent undesired changes to them or to the textiles treated due to the action of oxygen and other oxidative processes. This class of compounds includes, for example, substituted phenols, hydroquinones, pyrocatechols and aromatic amines as well as organic sulfides, polysulfides, dithiocarbamates, phosphites and phosphonates.

Additional use of antistatic agents gives better comfort for the wearer. Antistatic agents increase the surface conductivity, allowing charges to leak off better. External antistatic agents are usually substances with at least one hydrophilic molecular ligand. They provide a more or less hygroscopic film on the surface. These antistatic agents, usually surface-active, can be classified as nitrogenous (amines, amides, quaternary ammonium compounds), phosphor-containing (phosphoric acid esters) and sulfur-containing (alkyl sulfonates, alkyl sulfates) antistatic agents. Lauryl (or stearyl) dimethylbenzylammonium chlorides are likewise suitable as antistatic agents for textiles or as additives to laundry agents, in which case a softening effect is also produced.

Softening rinsers can be used for textile care and to improve the textile properties, such as a softer "hand" (softening) and reduced electrostatic charging (better wearer comfort). The active ingredients in softening rinsers are "esterquats", quaternary ammonium compounds with two hydrophobic groups, such as distearyldimethylammonium chloride, but those are increasingly being replaced by quaternary ammonium compounds that have ester groups in their hydrophobic groups as intended cleavage sites for biodegradation.

Such "esterquats" with better biodegradability are available, for instance, by esterifying mixtures of methyldiethanolamine and/or triethanolamine with fatty acids and then quaternizing the reaction products with alkylating agents in the known manner. Dimethylolethyleneurea is also a suitable finishing agent.

Silicone derivatives can be used to improve ability to absorb water and rewettability of the treated textiles, and to make ironing of the treated textiles easier. These also improve the ability of laundry detergents or cleaners to rinse out, due their foam-inhibiting properties. Examples of preferred silicone derivatives include polydialkyl or alkylaryl siloxanes, in which the alkyl groups have one to five C atoms and are partially or completely fluorinated. Preferred silicones include polydimethylsiloxanes, which can optionally be derivatized and are then aminofunctional or quaternized, or have Si—OH, Si—H and/or Si—Cl bonds. Other preferred silicones include the polyalkeneoxide-modified polysiloxanes, i. e., polysiloxanes having polyethylene glycols, for instance, and the polyalkylene oxide-modified dimethylpolysiloxanes.

Finally, UV absorbers can also be used according to the invention. They adsorb to the treated textiles and improve the light resistance of the fibers. Compounds that have these desired properties are, for example, the compounds that act by non-radiative deactivation and derivatives of benzophenone with substituents in the 2 and/or 4 position. Substituted benzotriazoles, acrylates phenyl-substituted in the 3 position (cinnamic acid derivatives), optionally with cyano groups in the 2 position, salicylates, organic nickel complexes and natural material such as umbelliferone and the body's own urocanic acid are also suitable.

Because of their fiber-protecting action, protein hydrolyzates are other preferred active substances from the field of laundry detergents or cleaners in the context of the present invention. Protein hydrolyzates are mixtures of products obtained by acid, basic, or enzyme-catalyzed degradations of proteins. Protein hydrolyzates of both plant and animal origin can be used according to the invention. Examples of animal protein hydrolyzates include elastin, collagen, keratin, silk and milk protein hydrolyzates, which can also be in the form of salts. According to the invention, use of protein hydrolyzates of plant origin, such as soy, almond, rice, pea, potato and wheat protein hydrolyzate, is preferred. Even though it is preferable to use protein hydrolyzates as such, amino acid mixtures or individual amino acids such as arginine, lysine, histidine or pyroglutamic acid can optionally be used instead. It is likewise possible to use derivatives of the protein hydrolyzates, as in the form of their fatty acid condensation products.

The non-aqueous solvents that can be used according to the invention include, in particular, the organic solvents, of which only the most important can be listed here: alcohols (methanol, ethanol, propanols, butanols, octanols, cyclohexanol), glycols (ethylene glycol, diethylene glycol), ethers and glycol ethers (diethyl ether, dibutyl ether, anisole, dioxane, tetrahydrofuran, mono, di, tri, polyethylene glycol ethers), ketones (acetone, butanone, cyclohexanone), esters (ethyl acetate, glycol esters), amides and other nitrogenous compounds (dimethylformamide, pyridine, N-methylpyrrolidone, acetonitrile), sulfur compounds (carbon disulfide, dimethylsulfoxide, sulfolan), nitro compounds (nitrobenzene), halohydrocarbons (dichloromethane, chloroform, tetrachloromethane, tri- and tetra-chloroethene, 1,2-dichloroethane, chlorofluorohydrocarbons), hydrocarbons (gasoline, petroleum ether, cyclohexane, methylcyclohexane, decalin, terpene solvents, benzene, toluene, xylenes). Alternatively, mixtures can for example be used instead of pure solvents, advantageously combining the solution properties of different solvents. One such solvent mixture that is especially preferred in the context of the present invention is, for instance, cleaner's naphtha, a mixture of different hydrocarbons suitable for chemical cleaning, preferably having more than 60% by weight of C12 to C14 hydrocarbons, especially preferably more than 80% by weight, and particularly more than 90% by weight, based in each case on the total weight of the mixture, preferably having a boiling point range of 81 to 110° C.

Other than where otherwise indicated, or where required to distinguish over the prior art, all numbers expressing quantities of ingredients herein are to be understood as modified in all instances by the term "about". As used herein, the words "may" and "may be" are to be interpreted in an open-ended, non-restrictive manner. At minimum, "may" and "may be" are to be interpreted as definitively including, but not limited to, the composition, structure, or act recited.

As used herein, and in particular as used herein to define the elements of the claims that follow, the articles "a" and "an" are synonymous and used interchangeably with "at least one" or "one or more," disclosing or encompassing both the singular and the plural, unless specifically defined herein otherwise. The conjunction "or" is used herein in both in the conjunctive and disjunctive sense, such that phrases or terms conjoined by "or" disclose or encompass each phrase or term alone as well as any combination so conjoined, unless specifically defined herein otherwise.

The description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed. Steps in any method disclosed or claimed need not be performed in the order recited, except as otherwise specifically disclosed or claimed or as needed to render such methods operative.

Changes in form and substitution of equivalents are contemplated as circumstances may suggest or render expedient. Although specific terms have been employed herein, such terms are intended in a descriptive sense and not for purposes of limitation.

EXAMPLE

A porous polymer carrier of cross-linked polypropylene was put into a Lödige mixer, combined with a melt of PEG (polyethylene glycol) 4000 and a perfume oil at 80° C., and mixed. The mixture solidified after about 1-2 minutes.

Resulting Composition of the Perfume Reservoir:

| | |
|---|---|
| cross-linked polypropylene | 48% by weight |
| PEG 4000 | 26% by weight |
| Perfume oil | 26% by weight |

What is claimed is:

1. A cosmetic composition, comprising:

a particulate fluid reservoir comprising a porous, particulate polymer substrate, said polymer comprising a crosslinked polyolefin, a fluoropolymer, or any copolymer or mixture thereof, said substrate having an at least partially open-pore structure with a mean pore diameter of 1 μm to 300 μm and being charged with 5% to 95% by weight, based on the weight of the charged polymer substrate, of an inclusion mixture, said inclusion mixture:

a) being highly viscous or solid at temperatures of ≦20° C.;

b) comprising a fluid and at least one additive that can flow at a temperature of 25° C. to 120° C., wherein the fluid further comprises one or more skin-care and/or skin-protective active substances;

c) transforming, essentially without decomposition, into a molten state at temperatures below 120° C.; and d) further comprising a solid selected from the group consisting of zeolite, bentonite, silicate, phosphate, urea, urea derivative, sulfate, carbonate, citrate, citric acid, acetate, anionic surfactant salt, and mixtures thereof.

2. The cosmetic composition of claim 1, wherein the fluid comprises a component selected from the group consisting of a liquid fragrance, a surfactant, a silicone oil, a paraffin, a liquid cosmetic ingredient, a liquid non-pharmaceutical additive, and mixtures thereof.

3. The cosmetic composition of claim 1, wherein the polymer substrate is hydrophobic.

4. The cosmetic composition of claim 1, wherein the inclusion mixture transforms essentially without decomposition into a molten state at a temperature below 100° C.

5. The cosmetic composition of claim 1, wherein the inclusion mixture comprises at least 20% by weight of the fluid and the additive.

6. The cosmetic composition of claim 1, wherein the additive at or near its melting or flow point is at least partially soluble in the fluid.

7. The cosmetic composition of claim 1, wherein the inclusion mixture is highly viscous or solid at temperatures ≦22° C.

8. The cosmetic composition of claim 7, wherein the inclusion mixture is highly viscous or solid at temperatures ≦38° C.

9. The cosmetic composition of claim 1, wherein the additive has a melting or flow point of 30 to 90° C.

10. The cosmetic composition of claim 1, wherein the inclusion mixture comprises up to 90% of the additive.

11. The cosmetic composition of claim 1, wherein the inclusion mixture comprises more than 5% by weight of the fluid.

12. The cosmetic composition of claim 1, wherein the inclusion mixture comprises less than 25% by weight of water, based on the entire fluid reservoir.

13. The cosmetic composition of claim 1, wherein the additive is at least one component selected from the group consisting of fatty alcohol, fatty acid, silicone, paraffin, nonionic surfactant, esterquat, mono-, di-, or tri-glyceride wax, carbohydrate, polyalkylene glycol, and mixtures thereof.

14. The cosmetic composition of claim 1, wherein the inclusion mixture comprises less than 50% by weight of the solid in component (d).

15. The cosmetic composition according to claim 14, wherein the solid in component (d) of the inclusion mixture has a d50 value of less than 0.2 mm.

16. The cosmetic composition according to claim 1, wherein the fluid reservoir further comprises a coating.

* * * * *